United States Patent
Gardella

(10) Patent No.: US 7,572,765 B2
(45) Date of Patent: Aug. 11, 2009

(54) CONFORMATIONALLY CONSTRAINED PARATHYROID HORMONE (PTH) ANALOGS

(75) Inventor: Thomas J. Gardella, Needham, MA (US)

(73) Assignee: The General Hospital Corporation, Boston, MA (US)

( * ) Notice: Subject to any disclaimer, the term of this patent is extended or adjusted under 35 U.S.C. 154(b) by 471 days.

(21) Appl. No.: 10/484,080

(22) PCT Filed: Jul. 19, 2002

(86) PCT No.: PCT/US02/22922

§ 371 (c)(1), (2), (4) Date: Jul. 6, 2004

(87) PCT Pub. No.: WO03/009804

PCT Pub. Date: Feb. 6, 2003

(65) Prior Publication Data

US 2005/0026839 A1   Feb. 3, 2005

Related U.S. Application Data

(60) Provisional application No. 60/326,212, filed on Oct. 2, 2001, provisional application No. 60/306,866, filed on Jul. 23, 2001.

(51) Int. Cl.
*A61K 38/29* (2006.01)

(52) U.S. Cl. .............................. 514/2; 514/13; 514/14; 514/15; 530/326; 530/327; 530/328

(58) Field of Classification Search ........................ None
See application file for complete search history.

(56) References Cited

U.S. PATENT DOCUMENTS

| | | |
|---|---|---|
| 5,393,869 A | 2/1995 | Nakagawa et al. |
| 5,496,801 A | 3/1996 | Holthuis et al. |
| 5,556,940 A | 9/1996 | Willick et al. |
| 5,616,560 A | 4/1997 | Geddes et al. |
| 5,693,616 A | 12/1997 | Krstenansky et al. |
| 5,695,955 A | 12/1997 | Krstenansky et al. |
| 5,717,062 A | 2/1998 | Chorev et al. |
| 5,723,577 A * | 3/1998 | Dong .................... 530/324 |
| 5,798,225 A | 8/1998 | Krstenansky et al. |
| 5,814,603 A | 9/1998 | Oldenburg et al. |
| 5,977,070 A | 11/1999 | Piazza et al. |
| 6,066,618 A | 5/2000 | Holick |
| 6,417,333 B1 | 7/2002 | Bringhurst et al. |
| 6,495,662 B1 | 12/2002 | Gardella et al. |
| 6,537,965 B1 | 3/2003 | Bringhurst et al. |
| 6,541,220 B1 | 4/2003 | Jüppner et al. |
| 6,803,213 B2 | 10/2004 | Bringhurst et al. |
| 2003/0144209 A1 | 7/2003 | Bringhurst et al. |
| 2003/0162256 A1 | 8/2003 | Jüppner et al. |
| 2003/0166838 A1 | 9/2003 | Gardella et al. |

FOREIGN PATENT DOCUMENTS

| | | |
|---|---|---|
| EP | 0 477 885 A2 | 4/1992 |
| WO | WO 87/01130 | 2/1987 |
| WO | WO 91/05050 | 4/1991 |
| WO | WO 92/01810 | 2/1992 |
| WO | WO 92/17602 | 10/1992 |
| WO | WO 95/11988 | 5/1995 |
| WO | WO 97/02834 | 1/1997 |
| WO | WO 98/05683 | 2/1998 |
| WO | WO 98/30590 A2 | 7/1998 |
| WO | WO 99/18945 | 4/1999 |
| WO | WO 00/23594 | 4/2000 |
| WO | WO 00/31137 | 6/2000 |
| WO | WO 00/31266 | 6/2000 |
| WO | WO 00/32771 | 6/2000 |
| WO | WO 00/32775 | 6/2000 |
| WO | WO 00/39278 | 7/2000 |
| WO | WO 00/40698 | 7/2000 |
| WO | WO 01/23427 | 4/2001 |

(Continued)

OTHER PUBLICATIONS

Luck et al. The (1-14) Fragment of Parathyroid Hormone PTH Activates Intact and Amino-Terminally Truncated PTH-1 Receptors. Mol. Endo. vol. 13, No. 5, pp. 670-680. 1999.*

(Continued)

*Primary Examiner*—Anish Gupta
(74) *Attorney, Agent, or Firm*—Clark & Elbing LLP

(57) ABSTRACT

The present invention relates to conformationally constrained parathyroid hormone (PTH) analogs, and methods of preparing and using the PTH analogs. The invention provides novel PTH polypeptide derivatives containing amino acid substitutions at selected positions in the polypeptides. The invention provides derivatives of PTH (1-34), PTH(1-21), PTH(1-20), PTH(1-19), PTH(1-18), PTH(1-17), PTH(1-16), PTH(1-15), PTH(1-14), PTH(1-13), PTH(1-12), PTH(1-11) and PTH (1-1 0) polypeptides, wherein at least one residue in each polypeptide is a helix, preferably an a-helix, stabilizing residue. The invention also provides methods of making such peptides. Further, the invention encompasses compositions and methods for use in limiting undesired bone loss in a vertebrate at risk of such bone loss, in treating conditions that are characterized by undesired bone loss or by the need for bone growth, e.g. in treating fractures or cartilage disorders and for raising cAMP levels in cells where deemed necessary.

40 Claims, 7 Drawing Sheets

FOREIGN PATENT DOCUMENTS

| WO | WO 01/23521 | 4/2001 |
|---|---|---|
| WO | WO 03/009804 | 2/2003 |
| WO | WO 2004/067021 | 8/2004 |
| WO | WO 2004/093902 | 11/2004 |
| WO | WO 2004/022830 | 2/2005 |

OTHER PUBLICATIONS

Bryant, S.D., et al., "Helix-Inducing α-Aminoisobutyric Acid in Opioid Mimetic Deltorphin C Analogues," *J. Med. Chem. 40*:2579-2587, American Chemical Society (1997).

Cervini, L.A., et al., "Human Growth Hormone-Releasing hGHRH(1-29)-NH$_2$: Systematic Structure-Activity Relationship Studies," *J. Med. Chem. 41*:717-727, American Chemical Society (1998).

Moretto, A., et al., "(αMe)Nva: stereoselective syntheses and preferred conformations of selected model peptides," *J. Pept. Res. 56*:283-297, Munksgaard International Publishers Ltd. (Nov. 2000).

Shimizu, N., et al., "Parathyroid Hormone (PTH)-(1-14) and -(1-11) Analogs Conformationally Constrained by α-Aminoisobutyric Acid Mediate Full Agonist Responses via the Juxtamembrane Region of the PTH-1 Receptor," *J. Biol. Chem. 276*:49003-49012, The American Society for Biochemistry and Molecular Biology, Inc. (Dec. 2001).

Supplementary European Search Report for European Application No. 02 77 8189, completed Oct. 4, 2005.

Abou-Samra, A-B., et al., "Expression cloning of a common receptor for parathyroid hormone and parathyroid hormone-related peptide from rat osteoblast-like cells: A single receptor stimulates intracellular accumulation of both cAMP and inositol triphosphates and increases intracellular free calcium," *Proc. Natl. Acad. Sci. USA 89*:2732-2736, National Academy of Sciences (1992).

Azarani, A., et al., "Structurally Diverse N-terminal Peptides of Parathyroid Hormone (PTH) and PTH-related Peptide (PTHRP) Inhibit the Na+/H+ Exchanger NHE3 Isoform by Binding to the PTH/PTHRP Receptor Type I and Activating Distinct Signaling Pathways," *J. Biol. Chem. 271*:14931-14936, The American Society for Biochemistry and Molecular Biology, Inc. (1996).

Bergwitz, C., et al., "Residues in the Membrane-spanning and Extracellular Loop Regions of the Parathyroid Hormone (PTH)-2 Receptor Determine Signaling Selective for PTH and PTH-related Peptide," *J. Biol. Chem. 272*:28861-28868, The American Society for Biochemistry and Molecular Biology, Inc. (1997).

Born, W. et al., "Inhibition of Parathyroid Hormone Bioactivity by Human Parathyroid Hormone (PTH)-(3-84) and PTH-(8-84) Synthesized in *Escherichia coli*," *Endocrinol. 123*:1848-1853, The Endocrine Society (1988).

Chakravarthy, B.R., et al., "Parathyroid Hormone Fragment [3-34] Stimulates Protein Kinase C (PKC) Activity in Rat Osteosarcoma and Murine T-Lymphoma Cells," *Biochem. Biophys. Res. Comm. 171*:1105-1110, Academic Press, Inc. (1990).

Chorev, M., et al., "Modifications of Position 12 in Parathyroid Hormone and Parathyroid Hormone Related Protein: Toward the Design of Highly Potent Antagonists," *Biochem. 29*:1580-1586, American Chemical Society (1990).

Civitelli, R., et al., "PTH elevates inositol polyphosphates and diacylglycerol in a rat osteoblast-like cell line," *Am. J. Physiol. 255*:E660-E667, American Physiological Society (1988).

Cohen, F.E., et al., "Analogues of Parathyroid Hormone Modified at Positions 3 and 6. Effects on Receptor Binding and Activation of Adenylyl Cyclase in Kidney and Bone," *J. Biol. Chem. 266*:1997-2004, The American Society for Biochemistry and Molecular Biology, Inc. (1991).

Cole, J.A., et al., "Regulation of Sodium-Dependent Phosphate Transport by Parathyroid Hormone in Opossum Kidney Cells: Adenosine 3', 5'-Monophosphate-Dependent and -Independent Mechanisms," *Endocrinol. 122*:2981-2989, The Endocrine Society (1988).

Cunningham, B.C., and Wells, J.A., "High-Resolution Epitope Mapping of hGH-Receptor Interactions by Alanine-Scanning Mutagenesis," *Science 244*:1081-1085, American Association for the Advancement of Science (1989).

Donahue, H.J., et al., "Differential Effects of Parathyroid Hormone and Its Analogues on Cytosolic Calcium Ion and cAMP Levels in Cultured Rat Osteoblast-like Cells," *J. Biol. Chem. 263*:13522-13527, The American Society for Biochemistry and Molecular Biology, Inc. (1988).

Dunlay, R., and Hruska, K., "PTH receptor coupling to phospholipase C is an alternate pathway of signal transduction in bone and kidney," *Am. J. Physiol. 258*:F223-F231, American Physiological Society (1990).

Fujimori, A., et al., "Structure-Function Relationship of Parathyroid Hormone: Activation of Phospholipase-C, Protein Kinase-A and -C in Osteosarcoma Cells," *Endocrinol. 130*:29-36, The Endocrine Society (1992).

Gaich, G., et al., "Amino-Terminal Parathyroid Hormone-Related Protein: Specific Binding and Cytosolic Calcium Responses in Rat Insulinoma Cells," *Endocrinol. 132*:1402-1409, The Endocrine Society (1993).

Gardella, T.J., et al., "Analysis of Parathyroid Hormone's Principal Receptor-Binding Region by Site-Directed Mutagenesis and Analog Design," *Endocrinol. 132*:2024-2030, The Endocrine Society (1993).

Gardella, T.J., et al., "Converting Parathyroid Hormone-related Peptide (PTHrP) into a Potent PTH-2 Receptor Agonist," *J. Biol. Chem. 271*:19888-19893, The American Society for Biochemistry and Molecular Biology, Inc. (1996).

Gardella, T.J., et al., "Determinants of [Arg2]PTH-(1-34) Binding and Signaling in the Transmembrane Region of the Parathyroid Hormone Receptor," *Endocrinol. 135*:1186-1194, The Endocrine Society (1994).

Gardella, T.J., et al., "Mutational Analysis of the Receptor-activating Region of Human Parathyroid Hormone," *J. Biol. Chem. 266*:13141-13146, The American Society for Biochemistry and Molecular Biology, Inc. (1991).

Gardella, T.J., et al., "Parathyroid Hormone (PTH)-PTH-related Peptide Hybrid Peptides Reveal Functional Interactions between the 1-14 and 15-34 Domains of the Ligand," *J. Biol. Chem. 270*:6584-6588, The American Society for Biochemistry and Molecular Biology, Inc. (1995).

Gardella, T.J., et al., "Transmembrane Residues of the Parathyroid Hormone (PTH)/PTH-related Peptide Receptor That Specifically Affect Binding and Signaling by Agonist Ligands," *J. Biol. Chem. 271*:12820-12825, The American Society for Biochemistry and Molecular Biology, Inc. (1996).

Goltzmann, D., et al., "Analysis of the Requirements for Parathyroid Hormone Action in Renal Membranes with the Use of Inhibiting Analogues," *J. Biol. Chem. 250*:3199-3203, The American Society for Biochemistry and Molecular Biology, Inc. (1975).

Gombert, F.O., et al., "Alanine and D-Amino Acid Scan of Human Parathyroid Hormone," in *Peptides: Chemistry, Structure and Biology. Proceedings of 14th American Peptide Symposium*, Jun. 18-23, Kaumaya, P.T.P., and Hodges, R.S., eds., Mayflower Scientific Ltd., Kingswinford, UK, pp. 661-662 (1996).

Guo, J., et al., "Parathyroid Hormone (PTH)/PTH-Related Peptide Receptor Density Modulates Activation of Phospholipase C and Phosphate Transport by PTH in LLC-PK1 Cells," *Endocrinol. 136*:3884-3891, The Endocrine Society (1995).

Hilliker, S., et al., "Truncation of the Amino Terminus of PTH Alters Its Anabolic Activity on Bone In Vivo," *Bone 19*:469-477, Elsevier Science (1996).

Horiuchi, N., et al., "A Parathyroid Hormone Inhibitor in vivo: Design and Biological Evaluation of a Hormone Analog," *Science 220*:1053-1055, American Association for the Advancement of Science (1983).

Hruska, K.A., et al., "Stimulation of Inositol Trisphosphate and Diacylglycerol Production in Renal Tubular Cells by Parathyroid Hormone," *J. Clin. Invest. 79*:230-239, The Rockefeller University Press (1987).

Iida-Klein, A., et al., "Mutations in the Second Cytoplasmic Loop of the Rat Parathyroid Hormone (PTH)/PTH-related Protein Receptor Result in Selective Loss of PTH-stimulated Phospholipase C Activity," *J. Biol. Chem.* 272:6882-6889, Tha American Society for Biochemistry and Molecular Biology, Inc. (1997).

Iida-Klein, A., et al., "Truncation of the Carboxyl-terminal Region of the Rat Parathyroid Hormone (PTH)/PTH-related Peptide Receptor Enhances PTH Stimulation of Adenylyl Cyclase but Not Phospholipase C," *J. Biol. Chem.* 270:8458-8465, The American Society for Biochemistry and Molecular Biology, Inc. (1995).

Jobert, A-S., et al., "Parathyroid Hormone-Induced Calcium Release from Intracellular Stores in a Human Kidney Cell Line in the Absence of Stimulation of Cyclic Adenosine 3',5'-Monophosphate Production," *Endocrinol.* 138:5282-5292, The Endocrine Society (1997).

Jouishomme, H., et al., "Further Definition of the Protein Kinase C Activation Domain of the Parathyroid Hormone," *J. Bone Min. Res.* 9:943-949, Mary Ann Liebert, Inc. (1994).

Joun, H., et al., "Tissue-Specific Transcription Start Sites and Alternative Splicing of the Parathyroid Hormone (PTH)/PTH-Related Peptide (PTHrP) Receptor Gene: A New PTH/PTHrP Receptor Splice Variant that Lacks the Signal Peptide," *Endocrinol.* 138:1742-1749, The Endocrine Society (1997).

Jüppner, H., et al., "A G Protein-Linked Receptor for Parathyroid Hormone and Parathyroid Hormone-Related Peptide," *Science* 254:1024-1026, American Association for the Advancement of Science (1991).

Jüppner, H., et al., "Properties of Amino-Terminal Parathyroid Hormone-Related Peptides Modified at Positions 11-13," *Peptides* 11:1139-1142, Pergamon Press (1990).

Jüppner, H., et al., "The Extracellular Amino-Terminal Region of the Parathyroid Hormone (PTH)/PTH-Related Peptide Receptor Determines the Binding Affinity for Carboxyl-Terminal Fragments of PTH-(1-34)," *Endocrinol.* 134:879-884, The Endocrine Society (1994).

Jüppner, H., et al., "The Parathyroid Hormone-like Peptide Associated with Humoral Hypercalcemia of Malignancy and Parathyroid Hormone Bind to the Same Receptor on the Plasma Membrane of ROS 17/2.8 Cells," *J. Biol. Chem.* 263:8557-8560, The American Society for Biochemistry and Molecular Biology, Inc. (1988).

Kong, X-F., et al., "The Rat, Mouse and Human Genes Encoding the Receptor for Parathyroid Hormone and Parathyroid Hormone-Related Peptide are Highly Homologous," *Biochem. Biophys. Res. Comm.* 200:1290-1299, Academic Press (1994).

Kovacs, C.S., et al., "Parathyroid hormone-related peptide (PTHrP) regulates fetal-placental calcium transport through a receptor distinct from the PTH/PTHrP receptor," *Proc. Natl. Acad. Sci. USA* 93:15233-15238, National Academy of Sciences (1996).

Lee, C., et al., "Homolog-Scanning Mutagenesis of the Parathyroid Hormone (PTH) Receptor Reveals PTH-(1-34) Binding Determinants in the Third Extracellular Loop," *Mol. Endocrinol.* 9:1269-1278, The Endocrine Society (1995).

Lee, C., et al., "Role of the Extracellular Regions of the Parathyroid Hormone (PTH)/PTH-Related Peptide Receptor in Hormone Binding," *Endocrin.* 135:1488-1495, The Endocrine Society (1994).

Mannstadt, M., et al., "Evidence for a Ligand Interaction Site at the Amino-Terminus of the Parathyroid Hormone (PTH)/PTH-related Protein Receptor from Cross-linking and Mutational Studies," *J. Biol. Chem.* 273:16890-16896, The American Society for Biochemistry and Molecular Biology, Inc. (1998).

Neugebauer, W., et al., "Solution Structure and Adenylyl Cyclase Stimulating Activities of C-Terminal Truncated Human Parathyroid Hormone Analogues," *Biochem.* 34:8835-8842, American Chemical Society (1995).

Nussbaum, S.R., et al., "Parathyroid Hormone•Renal Receptor Interactions. Demonstration of Two Receptor-Binding Domains," *J. Biol. Chem.* 255:10183-10187, The American Society for Biochemistry and Molecular Biology, Inc. (1980).

Nutt, R.F., et al., "Removal of Partial Agonism From Parathyroid Hormone (PTH)-Related Protein-(7-34)NH2 by Substitution of PTH Amino Acids at Positions 10 and 11," *Endocrinol.* 127:491-493, The Endocrine Society (1990).

Orloff, J.J., et al., "Analysis of PTHRP binding and signal transduction mechanisms in benign and malignant squamous cells," *Amer. J. Physiol.* 262:E599-E607, American Physiological Society (1992).

Orloff, J.J, et al., "Further Evidence for a Novel Receptor for Amino-Terminal Parathyroid Hormone-Related Protein on Keratinocytes and Squamous Carcinoma Cell Lines," *Endocrinol.* 136:3016-3023, The Endocrine Society 1995).

Orloff, J.J., et al., "A Midregion Parathyroid Hormone-Related Peptide Mobilizes Cytosolic Calcium and Stimulates Formation of Inositol Triphosphate in a Squamous Carcinoma Cell Line," *Endocrinol.* 137:5376-5385, The Endocrine Society (1996).

Plotkin, H., et al., "Dissociation of Bone Formation from Resorption during 2-Week Treatment with Human Parathyroid Hormone-Related Peptide-(1-36) in Humans: Potential as an Anabolic Therapy for Osteoporosis," *J. Clin. Endocrinol. Metabol.* 83:2786-2791, The Endocrine Society (1998).

Potts, Jr., J.T., et al., "Structure based design of parathyroid hormone analogs," *J. Endocrinol.* 154:S15-S21, The Endocrine Society (1997).

Reid, I.R., et al., "Parathyroid hormone acutely elevates intracellular calcium in osteoblastlike cells," *Am. J. Physiol.* 253:E45-E51, American Physiological Society (1987).

Rixon, R.H., et al., "Parathyroid Hormone Fragments May Stimulate Bone Growth in Ovariectomized Rats by Activating Adenylyl Cyclase," *J. Bone Min. Res.* 9:1179-1189, Mary Ann Liebert, Inc. (1994).

Roe, E.B., et al., "Parathyroid Hormone 1-34 (hPTH 1-34) and Estrogen Produce Dramatic Bone Density Increases in Postmenopausal Osteoporosis—Results from a Placebo-Controlled randomized Trial," *J. Bone. Miner. Res.* 14:S137 Abs. 1019, American Society for Bone and Mineral Research (1999).

Schipani, E., et al., "Identical Complementary Deoxyribonucleic Acids Encode a Human Renal and Bone Parathyroid Hormone (PTH)/PTH-Related Peptide Receptor," *Endocrinol.* 132:2157-2165, The Endocrine Society (1993).

Schneider, H., et al., "A C-terminally truncated human parathyroid hormone receptor is functional and activates multiple G proteins," *FEBS Letts.* 351:281-285, Elsevier Science (1994).

Schneider, H., et al., "Cloning and functional expression of a human parathyroid hormone receptor," *Eur. J. Pharmacol.* 246:149-155, Elsevier Science B.V. (1993).

Segre, G.V., et al., "Characterization of Parathyroid Hormone Receptors in Canine Renal Cortical Plasma Membranes Using a Radioiodinated Sulfur-free Hormone Analogue," *J. Biol. Chem.* 254:6980-6986, The American Society of Biological Chemists Inc. (1979).

Seuwen, K., and Boddeke, H.G.W.M., "Heparin-insensitive calcium release from intracellular stores triggered by the recombinant human parathyroid hormone receptor," *Br. J. Pharmacol.* 114:1613-1620, Stockton Press (1995).

Shen, V., et al., "Effects of Combined and Separate Intermittent Administration of Low-Dose Human Parathyroid Hormone Fragment (1-34) and 17β-Estradiol on Bone Histomorphometry in Ovariectomized Rats with Established Osteopenia," *Calcif. Tissue Int.* 50:214-220, Springer-Verlag (1992).

Shimizu, M., et al., "Minimization of Parathyroid Hormone. Novel Amino-Terminal Parathyroid Hormone Fragments with Enhanced Potency in Activating the Type 1 Parathyroid Hormone Receptor," *J. Biol. Chem.* 275:21836-21843, The American Society for Biochemistry and Molecular Biology, Inc. (Jul. 2000).

Shimizu, M., et al., "Type-Substitution Analysis of the Amino-Terminal Fragment of Parathyroid Hormone, PTH(1-14): An Approach toward New Low Molecular Weight PTH Agonists," *J. Bone Min. Res.* 14(Suppl. 1):S289, Abstract F398, Mary Ann Liebert, Inc. (1999).

Shunkunami, C., et al., "Chondrongenic Differentiation of Clonal Mouse Embryonic Cell Line ATDC5 In Vitro: Differentiation-dependent Gene Expression of Parathyroid Hormone (PTH)/PTH-related Peptide Receptor," *J. Cell Biol.* 133:457-468, Rockefeller University Press (1996).

Slovik, D.M., et al., "Restoration of Spinal Bone in Osteoporotic Men by Treatment With Human Parathyroid Hormone (1-34) and 1,25-Dihydroxyvitamin D," *J. Bone Min. Res.* 1:377-381, Mary Ann Liebert, Inc. (1986).

Suva, L.J., et al., "A Parathyroid Hormone-Related Protein Implicated in Malignant Hypercalcemia: Cloning and Expression," *Science 237*:893-896, American Association for the Advancement of Science (1987).

Takasu, H., and Bringhurst, P.R., "Type-1 Parathyroid Hormone (PTH)/PTH-Related Peptide (PTHrP) Receptors Activate Phospholipase C in Response to Carboxyl-Truncated Analogs of PTH(1-34)," *Endocrinol. 139*: :4293-4299, The Endocrine Society (1998).

Takasu, H., et al., "Amino-Terminal Modifications of Human Parathyroid Hormone (PTH) Selectively Alter Phospholipase C Signaling via the Type 1 PTH Receptor: Implications for Design of Signal-Specific PTH Ligands," *Biochem. 38*:13453-13460, American Chemical Society (1999).

Takasu, H., et al., "Dual Signaling and Ligand Selectivity of the Human PTH/PTHrP Receptor," *J. Bone Min. Res. 14*:11-20, Blackwell Science, Inc. (1999).

Takasu, H., et al., "The 69-84 Amino Acid Region of the Parathyroid Hormone Molecule Is Essential for the Interaction of the Hormone with the Binding Sites with Carboxyl-Terminal Specificity," *Endocrinol. 137*:5537-5543, The Endocrine Society (1996).

Tamura, T., et al., "Parathyroid Hormone 1-34, But Not 3-34 or 7-34, Transiently Translocates Protein Kinase C in Cultured Renal (OK) Cells," *Biochem. Biophys. Res. Comm. 159*:1352-1358, Academic Press, Inc. (1989).

Tregear, G.W., and Potts, Jr., J.T., "Synthetic Analogues of Residues 1-34 of Human Parathyroid Hormone: Influence of Residue No. 1 on Biological Potency In Vitro," *Endocrine Res. Comm. 2*:561-570, Marcel Dekker, Inc. (1975).

Turner, P.R., et al., "Single Mutations Allow the PTH2 Receptor to respond to PTHrP," *J. Bone Min. Res. 12*:S133, Abstract 121, Blackwell Science, Inc. (1997).

Turner, P.R., et al., "Transmembrane Residues Together with the Amino Terminus Limit the Response of the Parathyroid Hormone (PTH) 2 Receptor to PTH-related Peptide," *J. Biol. Chem. 273*:3830-3837, The American Society for Biochemistry and Molecular Biology, Inc. (1998).

Ureña, P., et al., "Regulation of Parathyroid Hormone (PTH)/PTH-Related Peptide Receptor Messenger Ribonucleic Acid by Glucocorticoids and PTH in ROS 17/2.8 and OK Cells," *Endocrinol. 134*:451-456, the Endocrine Society (1994).

Usdin, T.B., et al., "Identification and Functional Expression of a Receptor Selection Recognizing Parathyroid Hormone, the PTH2 Receptor," *J. Biol. Chem. 270*:15455-15458, The American Society for Biochemistry and Molecular Biology, Inc. (1995).

Whitfield, J.F., et al., "Stimulation of the Growth of Femoral Trabecular Bone in Ovariectomized Rats by the Novel Parathyroid Hormone Fragment, hPTH-(1-31)NH2 (Ostabolin)," *Calcif. Tissue Int. 58*:81-87, Springer-Verlag (1996).

Wu, T.L., et al., "Structural and Physiologic Characterization of the Mid-region Secretory Species of Parathyroid Hormone-related Protein," *J. Biol. Chem. 271*:24371-24381, The American Society for Biochemistry and Molecular Biology, Inc. (1996).

Yamamoto, S., et al., "Centrally Administered Parathyroid Hormone (PTH)-Related Protein (1-34) But Not PTH(1-34) Stimulates Arginine-Vasopressin Secretion and Its Messenger Ribonucleic Acid Expression in Supraoptic Nucleus of the Conscious Rats", *Endocrinol. 139*:383-388, The Endocrine Society (1998).

Yamamoto, S., et al., "Parathyroid Hormone-Related Peptide-(1-34) [PTHrP-(1-34)] Induces Vasopressin Release from the Rat Supraoptic Nucleus in Vitro through a Novel Receptor Distinct from a Type I or Type II PTH/PTHrP Receptor," *Endocrinol. 138*:2066-2072, The Endocrine Society (1997).

Zhou, A.T., et al., "Direct mapping of an agonist-binding domain within the parathyroid hormone/parathyroid hormone-related protein receptor by photoaffinity crosslinking," *Proc. Natl. Acad. Sci. USA 94*:3644-3649, National Academy of Sciences (1997).

U.S. Appl. No. 09/475,158, Gardella, et al., filed Dec. 30, 1999 (not Published).

U.S. Appl. No. 09/672,020, Gardella, et al., filed Sep. 29, 2000 (not Published).

U.S. Appl. No. 09/869,565, Kronenberg et al., filed Jun. 29, 2001, (not Published) U.S. National Phase of WO 00/40698, Document AT5.

U.S. Appl. No. 10/959,605, Bringhurst et al., filed Oct. 7, 2004 (not Published).

* cited by examiner

(delNt)

(SaOS-2)

(metatarsal)

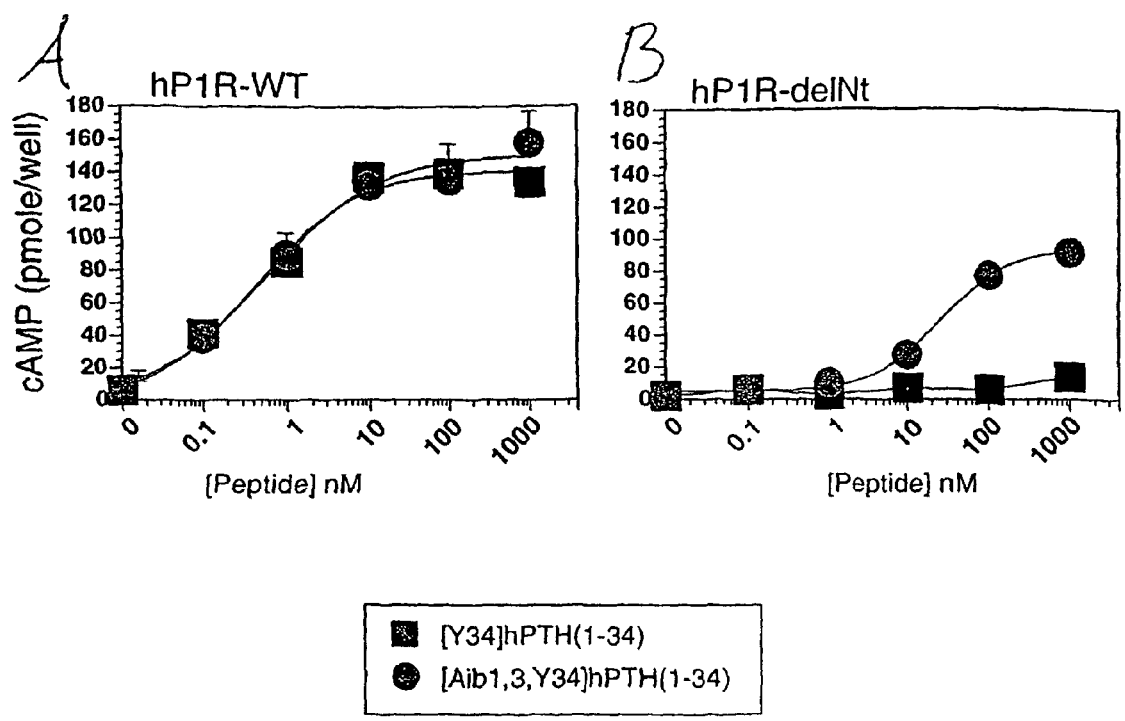

CONFORMATIONALLY CONSTRAINED PARATHYROID HORMONE (PTH) ANALOGS

BACKGROUND OF THE INVENTION

1. Field of the Invention

The present invention relates to conformationally constrained parathyroid hormone (PTH) analogs, and methods of preparing and using the PTH analogs.

2. Background Art

Parathyroid Hormone

Parathyroid hormone (PTH), an 84 amino acid peptide, is the principal regulator of ionized blood calcium in the human body (Kronenberg, H. M., et al., In *Handbook of Experimental Pharmacology*, Mundy, G. R., and Martin, T. J., (eds), pp. 185-201, Springer-Verlag, Heidelberg (1993)). Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH is thought to exert these effects primarily through receptor-mediated activation of adenylate cyclase and/or phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a parathyroid gland lesion (e.g., adenoma, hyperplasia, or carcinoma). Another type of hypercalcemia, humoral hypercalcemia of malignancy (HHM) is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues.

Osteoporosis

Osteoporosis is a potentially crippling skeletal disease observed in a substantial portion of the senior adult population, in pregnant women and even in juveniles. The term osteoporosis refers to a heterogeneous group of disorders. Clinically, osteoporosis is separated into type I and type II. Type I osteoporosis occurs predominantly in middle aged women and is associated with estrogen loss at menopause, while osteoporosis type II is associated with advancing age. Patients with osteoporosis would benefit from new therapies designed to promote fracture repair, or from therapies designed t6 prevent or lessen the fractures associated with the disease.

The disease is marked by diminished bone mass, decreased bone mineral density (BMD), decreased bone strength and an increased risk of bone fracture. At present, there is no effective cure for osteoporosis, though estrogen, calcitonin and the bisphosphonates, etidronate and alendronate are used to treat the disease with varying levels of success. These agents act to decrease bone resorption. Since parathyroid hormone regulates blood calcium and the phosphate levels, and has potent anabolic (bone-forming) effects on the skeleton, in animals (Shen, V., et al., *Calcif Tissue Int.* 50:214-220 (1992); Whitefild, J. F., et al., *Calcif Tissue Int.* 56:227-231 (1995) and Whitfield, J. F., et al., *Calcif Tissue Int.* 60:26-29 (1997)) and humans (Slovik, D. M., et al., *J. Bone Miner. Res.* 1:377-381 (1986); Dempster, D. W., et al., *Endocr. Rev.* 14:690-709 (1993) and Dempster, D. W., et al., *Endocr. Rev.* 15:261 (1994)) when administered intermittently, PTH, or PTH derivatives, are prime candidates for new and effective therapies for osteoporosis.

PTH Derivatives

PTH derivatives include polypeptides that have amino acid substitutions or are truncated relative to the full length molecule. Both a 14 and a 34 amino acid amino-terminal truncated form of PTH, as well as a C-terminal truncated form have been studied. Additionally, amino acid substitutions within the truncated polypeptides have also been investigated.

Synthetic PTH(1-34) exhibits full bioactivity in most cell-based assay systems, has potent anabolic effects on bone mass in animals and has recently been shown to reduce the risk of bone fracture in postmenopausal osteoporotic women (Neer, R. M., et al., *N.E.J.M.* 344:1434-1441 (2001); Dempster, D. W., et al., *Endocr Rev* 14:690-709 (1993)). PTH acts on the PTH/PTHrP receptor (P1R), a class II G protein-coupled heptahelical receptor that couples to the adenylyl cyclase/CAMP and phospolipase C/inositol phosphate (IP) signaling pathway (Rippner, H., et al., *Science* 254:1024-1026 (1991)). Deletion analysis studies have shown that the amino-terminal residues of PTH play a crucial role in stimulating the P1 R to activate the cAMP and IP signaling pathways (Tregear, G. W., et al., *Endocrinology* 93:1349-1353 (1973); Takasu, H., et al., *Biochemistry* 38:13453-13460 (1999)). Crosslinking and receptor mutagenesis studies have indicated that residues in the amino-terminal portion of PTH interact with the extracellular loops and extracellular ends of the seven transmembrane helices, which reside within the juxtamembrane region of the receptor (Bergwitz, C., et al., *J. Biol. Chem.* 271:26469-26472 (1996); Hoare, S. R. J., et al., *J. Biol. Chem* 276:7741-7753 (2001); Behar, V., et al., *J. Biol. Chem.* 275:9-17 (1999); Shimizu, M., et al., *J. Biol. Chem.* 275:19456-19460(2000); Luck, M. D., et al., *Molecular Endocrinology* 13:670-680 (1999)).

BRIEF SUMMARY OF THE INVENTION

The invention provides novel PTH polypeptide derivatives containing amino acid substitutions at selected positions in the polypeptides. The derivatives function as full, or nearly full, agonists of the PTH-1 receptor. Because of their unique properties, these polypeptides have a utility as drugs for treating human diseases of the skeleton, such as osteoporosis.

The invention provides derivatives of PTH(1-21), PTH(1-20), PTH(1-19), PTH(1-18),PTH(1-17), PTH(1-16), PTH(1-15), PTH(1-14), PH(1-13), PTH(1-12), PTH(1-11) and PTH (1-10) polypeptides, wherein at least one residue in each polypeptide is a helix, preferably an α-helix, stabilizing residue. The invention also provides methods of making such peptides. Further, the invention encompasses compositions and methods for use in limiting undesired bone loss in a vertebrate at risk of such bone loss, in treating conditions that are characterized by undesired bone loss or by the need for bone growth, e.g. in treating fractures or cartilage disorders and for raising cAMP levels in cells where deemed necessary.

In one aspect, the invention is directed to a biologically active peptide consisting essentially of $X_{01}$ ValX$_{02}$GluIleGlnLeuMetHisX$_{03}$X$_{04}$X$_{05}$X$_{06}$X$_{07}$ (SEQ ID NO: 1), wherein $X_{01}$ is an α-helix-stabilizing residue, desaminoGly, desaminoSer or desaminoAla; $X_{02}$ is an α-helix-stabilizing residue, Ala, or Ser; $X_{03}$ is Ala, Gln or Asn; $X_{04}$ is Arg, Har or Leu; $X_{05}$ is an α-helix-stabilizing residue, Ala or Gly; $X_{06}$ is an α-helix-stabilizing residue or Lys; and $X_{07}$ is an α-helix-stabilizing residue, Trp or His: and wherein at least one of $X_{01}$, $X_{02}$, $X_{03}$, $X_{04}$, $X_{05}$, $X_{06}$ or $X_{07}$ is an α-helix-stabilizing residue.

In another aspect, the invention relates to SEQ ID NO: 1, wherein the α-helix-stabilizing amino acid is selected from the group consisting of Aib, ACPC (1-aminocyclopropylcarboxylic acid), DEG (diethylglycine) and 1-aminocyclopentanecarboxylic acid. In another aspect, the invention relates to SEQ ID NO: 1, wherein the α-helix-stabilizing amino acid is Aib.

The invention is further drawn to fragments of the peptide of SEQ ID NO: 1, in particular $X_{01}$ ValX$_{02}$GluIleGlnLeuMetHisX$_{03}$X$_{04}$X$_{05}$X$_{06}$ (SEQ ID NO: 12), $X_{01}$ ValX$_{02}$GluIleGlnLeuMetHisX$_{03}$X$_{04}$X$_{05}$ (SEQ ID NO: 13), $X_{01}$ ValX$_{02}$GluIleGlnLeuMetHisX$_{03}$X$_{04}$ (SEQ ID NO: 14) and $X_{01}$ ValX$_{02}$GluIleGlnLeuMetHisX$_{03}$ (SEQ ID NO: 15). The invention further encompasses pharmaceutically acceptable salts of the above-described peptides, and N- or C-derivatives of the peptides. A preferable embodiment of the invention is drawn to any of the above recited polypeptides, wherein the polypeptide contains a C-terminal amnide.

In addition, the invention is drawn to a biologically active polypeptide consisting essentially of AibValAibGluIleGlnLeuNleHisGlnHarAlaLysTrpLeu-AlaSerValArgArtTyr (SEQ ID NO. 8); fragments thereof, containing amino acids 1-20, 1-19, 1-18, 1-17, 1-16 or 1-15; pharmaceutically acceptable salts thereof; or N- or C-derivatives thereof.

The invention is further drawn to any of the above polypeptides labeled with a label selected from the group consisting of: a radiolabel, a flourescent label, a bioluminescent label, or a chemiluminescent label. In a preferable embodiment the radiolabel is $^{125}$I or $^{99m}$Tc.

Preferred embodiments of the biologically active peptide include: AibValSerGluIleGlnLeuMetHisAsnLeuGlyLysHis (SEQ ID NO. 2); desamino -AlaValAibGluIleGlnLeuMetHisAsnLeuGlyLysHis (SEQ ID NO. 3); desamino-SerValAibGluIleGlnLeuMetHisAsnLeuGlyLysHis (SEQ ID NO. 4); desamino-GlyValAibGluIleGlnLeuMetHisAsnLeuGlyLysHis (SEQ ID NO. 5); AibValAibGluIleGlnLeuMetHisGlnHarAlaLysTrp (SEQ ID NO. 6); AibValAibGluIleGlnLeuMetHisAsnLeuGlyLysHis (SEQ ID NO. 7); AibValAlaGluIleGlnLeuMetHisGlnHarAlaLysTrp (SEQ ID NO. 9); AlaValAibGluIleGlnLeuMetHisGlnHarAlaLysTrp (SEQ ID NO. 10); SerValAibGluIleGffi uMetHisGlnHarAlaLysTrp (SEQ ID NO. 11); and AibValAibGluIleGlnLeuMetHisGlnHar (SEQ ID NO. 16). It is contemplated that fragments of the above mentioned peptides, containing amino acids 1-10, 1-11, 1-12 or 1-13, are also embodiments of the present invention. The invention further encompasses pharmaceutically acceptable salts of the above-described peptides, and N- or C-derivatives of the peptides.

Other constrained amino acids that are substituted for Aib are ACPC (1-aminocyclopropylcarboxylic acid), DEG (diethylglycine) and 1-aminocyclopentanecarboxylic acid.

In accordance with yet a further aspect of the invention, this invention also provides pharmaceutical compositions comprising a PTH derivative and a pharmaceutically acceptable excipient and/or a pharmaceutically acceptable solution such as saline or a physiologically buffered solution.

This invention also provides a method for treating mammalian conditions characterized by decreases in bone mass, which method comprises administering to a subject in need thereof an effective bone mass-increasing amount of a biologically active PTH polypeptide. A preferable embodiment of the invention is drawn to conditions such as osteoporosis. The types of osteoporosis include, but are not limited to old age osteoporosis and postmenopausal osteoporosis. Additional preferable embodiments include using an effective amounts of the polypeptide of about 0.01 µg/kg/day to about 1.0 µg/kg/day wherein the polypeptide is administered parenterally, subcutaneously or by nasal insufflation.

In accordance with yet a further aspect of the invention, this invention also provides a method for determining rates of bone reformation, bone resorption and/or bone remodeling comprising administering to a patient an effective amount of a labeled PTH polypeptide, such as for example, SEQ ID NO: 1 or a derivatives thereof and determining the uptake of the peptide into the bone of the patient. The peptide is labeled with a label selected from the group consisting of: radiolabel, flourescent label, bioluminescent label, or chemiluminescent label. An example of a suitable radiolabel is $^{99m}$Tc.

The invention is further related to a method of increasing cAMP in a mammalian cell having PTH-1 receptors, the method comprising contacting the cell with a sufficient amount of the polypeptide of the invention to increase cAMP.

The invention also provides derivatives of rat PTH(1-34) (rPTH(1-34)) given by AlaValSerGluIleGlnLeuMetHisAsnLeuGlyLysHisLeuAlaSerValGluArg MetGlnTrpLeuArgLysLysLeuGlnAspValHisAsnPhe (SEQ ID NO: 30), and of human PTH(1-34) (hPTH(1-34)) given by SerValSerGluIleGlnLeuMetHisAsn LeuGlyLysHisLeuAsnSerMetGluArgValGluTrpLeuArgLysLysLeuGlnAspVal HisAsnPhe (SEQ ID NO: 31).

In another aspect, the invention relates to a biologically active peptide consisting essentially of the formula $X_{01}$ ValX$_{02}$GluIleGlnLeuX$_{03}$HisX$_{04}$X$_{05}$X$_{06}$X$_{07}$X$_{08}$LeuX$_{09}$Ser X$_{10}$X$_{11}$ArgX$_{12}$X$_{13}$TrpLeuArgLysLysLeuGlnAspValHisAsn X$_{14}$ (SEQ ID NO: 19) wherein $X_{01}$ is an α-helix-stabilizing residue, desaminoGly, desaminoSer or desaminoAla; $X_{02}$ is an α-helix-stabilizing residue, Ala, or Ser; $X_{03}$ is Met or Nle; $X_{04}$ is Ala, Gln or Asn; $X_{05}$ is Arg, Har or Leu; $X_{06}$ is an α-helix-stabilizing residue, Ala or Gly; $X_{07}$ is an α-helix-stabilizing residue or Lys; $X_{08}$ is an α-helix-stabilizing residue, Trp or His; $X_{09}$ is Ala or Asn; $X_{10}$ is Met or Val; $X_{11}$ is Arg or Glu; $X_{12}$ is Met or Val; $X_{13}$ is Gln or Glu; $X_{14}$ is Tyr or Phe; and wherein at least one of $X_{01}$, $X_{02}$, $X_{06}$, $X_{7}$, or $X_{08}$ is an α-helix-stabilizing residue. The invention also relates to fragments thereof, containing amino acids 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, or 1-11. The invention also relates to pharmaceutically acceptable salts and N- or C-derivatives of SEQ ID NO: 19 or the above described fragments.

In another aspect, the invention relates to SEQ ID NO: 19, wherein the α-helix-stabilizing amino acid is selected from the group consisting of Aib, ACPC (1-aminocyclopropylcarboxylic acid), DEG (diethylglycine) and 1-aminocyclopropylcarboxylic acid. In another aspect, the invention relates to SEQ ID NO: 19, wherein the α-helix-stabilizing amino acid is Aib.

In another aspect, the invention relates specifically to the following peptides: AibValSerGluIleGlnLeuMetHisAsnLeuGlyLysHisLeuX$_{09}$ Ser$_{10}$X$_{11}$Arg X$_{12}$X$_{13}$TrpLeuArgLysLysLeuGlnAspValHisAsnX$_{14}$ (SEQ ID NO. 20); desaminoAlaValAibGluIleGlnLeuMetHisAsnLeuGlyLysHis LeuX$_{09}$SerX$_{10}$X$_{11}$ArgX$_{12}$X$_{13}$Trp LeuArgLysLysLeuGlnAspValHisAsnX$_{14}$ (SEQ ID NO. 21); desaminoSerValAibGluIleGlnLeuMetHisAsnLeuGlyLysHis LeuX$_{09}$SerX$_{10}$X$_{11}$ArgX$_{12}$X$_{13}$Trp LeuArgLysLysLeuGlnAspValHisAsnX$_{14}$ (SEQ ID NO. 22); desaminoGlyValAibGluIleGlnLeuMetHisAsnLeuGlyLysHisLeu X$_{09}$SerX$_{10}$X$_{11}$ArgX$_{12}$X$_{13}$Trp LeuArgLysLysLeuGlnAspValHisAsnX$_{14}$ (SEQ ID NO. 23); AibValAibGluIleGlnLeuMetHisGlnHarGlyLysTrpLeuX$_{09}$ Ser X$_{10}$X$_{11}$ArgX$_{12}$X$_{13}$Trp LeuArgLysLysLeuGlnAspValHisAsnX$_{14}$ (SEQ ID NO. 24); AibValAibGluIleGlnLeuMetHisAsnLeuGlyLysHisLeuX$_{09}$ Ser X$_{10}$X$_{11}$ArgX$_{12}$X$_{13}$Trp LeuArgLysLysLeuGlnAspValHisAsnX$_{14}$ (SEQ ID NO. 25); AibValAlaGluIleGlnLeuMetHisGlnHarAlaLysTrpLeuX$_{09}$ SerX$_{10}$X$_{11}$ArgX$_{12}$X$_{13}$Trp LeuArgLysLysLeuGlnAspValHisAsnX$_{14}$ (SEQ ID NO. 26); AlaValAibGluIleGlnLeuMetHisGlnHarAlaLysTrpLeuX$_{09}$ SerX$_{10}$X$_{11}$ArgX$_{12}$X$_{13}$ TrpLeuArgLysLysLeuGlnAspValHisAsn X$_{14}$ (SEQ ID NO. 27); and SerValAibGluIleGlnLeuMetHisGlnHarAlaLysTrpLeu X$_{09}$Ser X$_{10}$X$_{11}$ArgX$_{12}$X$_{13}$Trp LeuArgLysLysLeuGlnAspValHisAsnX$_{14}$ (SEQ ID NO. 28). X$_{09}$, X$_{10}$, X$_{11}$, X$_{12}$, X$_{13}$ and X$_{14}$ have the same meaning as defined for SEQ ID NO: 19. The invention also relates to pharmaceutically acceptable salts or N- or C-derivatives of the above peptides.

The invention also relates to a biologically active peptide consisting essentially of the formula AibValAibGluIleGlnLeuNleHisGlnHarAlaLysTrpLeu AlaSerValArgArgX$_{12}$X$_{13}$TrpLeuArgLysLysLeuGlnAspVal HisAsnX$_{14}$ (SEQ ID NO: 29) wherein X$_{12}$ is Met or Val; X$_{13}$ is Gln or Glu; and X$_{14}$ is Tyr or Phe. The invention also relates to pharmaceutically acceptable salts or N- or C-derivatives of SEQ ID NO: 29. The invention also relates to fragments thereof, containing amino acids 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, or 1-11.

In another aspect of the invention, SEQ ID NO: 19, SEQ ID NO: 29 or any of the above peptides are labeled. In another aspect of the invention, SEQ ID NO: 19, SEQ ID NO: 29 or any of the above peptides are labeled with a fluorescent label, a chemiluminescent label; a bioluminescent label; a radioactive label; $^{125}$I; or $^{99m}$Tc.

In another aspect, the invention is directed to a pharmaceutical composition comprising the biologically active peptide SEQ ID NO: 19, SEQ ID NO: 29 or any of the above peptides, and a pharmaceutically acceptable carrier.

In another aspcet, the invention is directed to a method for treating mammalian conditions characterized by decreases in bone mass, the method comprising administering to a subject in need thereof an effective bone mass-increasing amount of a biologically active peptide of SEQ ID NO: 19, SEQ ID NO: 29 or any of the above peptides.

In another aspcet, the invention is directed to a method for treating mammalian conditions characterized by decreases in bone mass, the method comprising administering to a subject in need thereof an effective bone mass-increasing amount of a composition comprising a biologically active peptide of SEQ ID NO: 19, SEQ ID NO: 29 or any of the above peptides and a pharmaceutically acceptable carrier.

In another aspect of the invention, the condition to be treated is osteoporosis, old age osteoporosis, or post-menopausal osteoporosis. In another aspect of the invention, the effective amount of SEQ ID NO: 19, SEQ ID NO: 29 or any of the above peptides for increasing bone mass is from about 0.01 µg/kg/day to about 1.0 µg/kg/day. In another aspect of the invention, the method of administration is parenteral, subcutaneous or nasal insufflation.

In another aspcet, the invention is directed to a method for determining rates of bone reformation, bone resorption and/or bone remodeling comprising administering to a patient an effective amount of SEQ ID NO: 19, SEQ ID NO: 29 or any of the above peptides and determining the uptake of the peptide into the bone of the patient.

In another aspcet, the invention is directed to a method of making SEQ ID NO: 19, SEQ ID NO: 29 or any of the above peptides, wherein the peptide is synthesized by solid phase synthesis. in another aspcet, the invention is directed to a method of making SEQ ID NO: 19, SEQ ID NO: 29 or any of the above peptides, wherein the peptide is protected by FMOC.

BRIEF DESCRIPTION OF THE FIGURES

FIG. 7. Signaling and binding properties of hPTH(1-34) analogs in COS-7 cells expressing wildtype P1R (hP1R-WT, FIG. 7A) and N-terminally truncated P1R (hP1R-delNT, FIG. 7B). The COS-7 cells were used to evaluate the capacities of the indicated PTH analogs to stimulate intracellular cAMP accumulation. Cells expressing hP1R-delNT were prepared as described above. Peptides and corresponding symbols are identified in the key.

DETAILED DESCRIPTION OF THE INVENTION

Definitions

Figure 1:
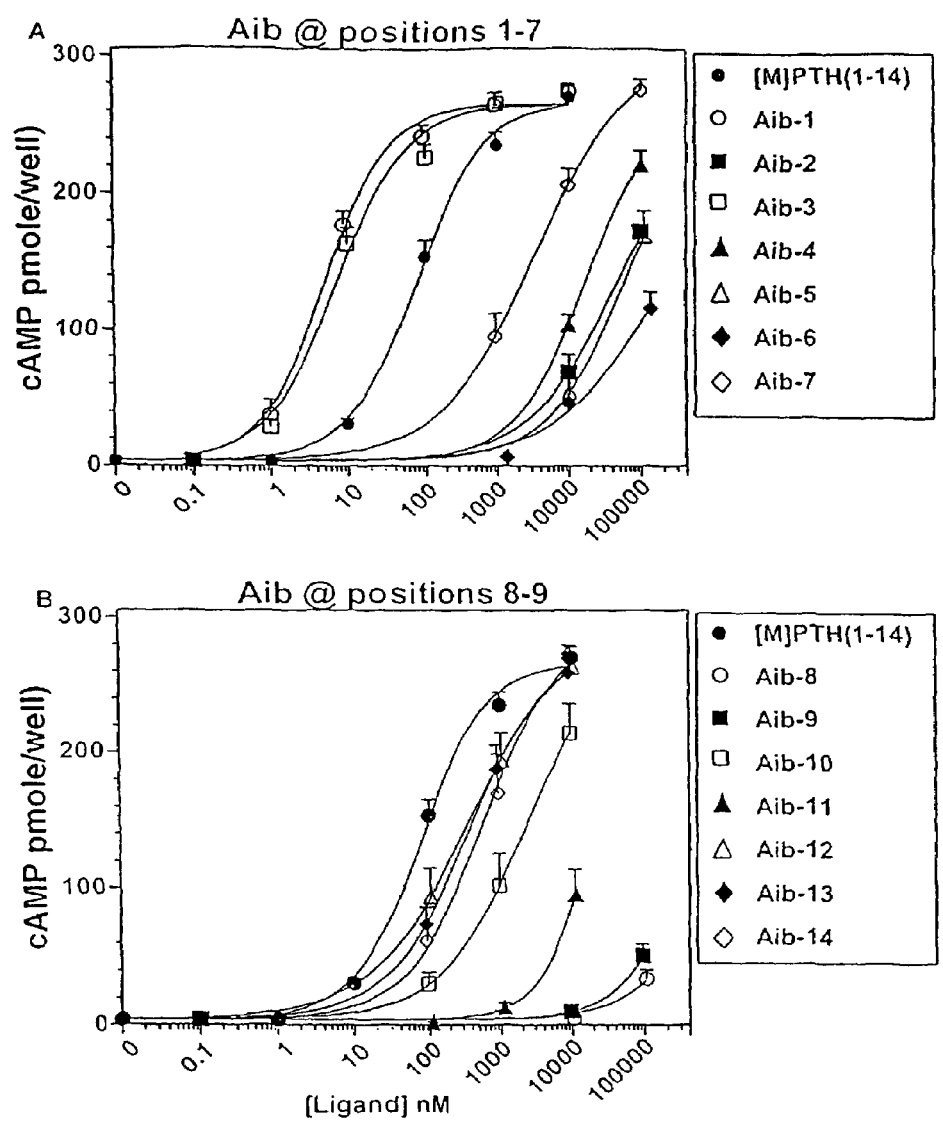
FIG. 1. Aib-scan of a modified PTH(1-14) analog in HKRK-B28 cells. The peptide [Ala$^{3,12}$,Gln$^{10}$,Har$^{11}$,Trp$^{14}$] PTH(1-14) amide {[M]PTH(1-14)}, and derivatives of that peptide containing a single Aib substitution at one of each residue position, were evaluated for the capacity to stimulate intracellular cAMP accumulation in HKRK-B28 cells. The peptides with substitutions at position 1-7 are shown in panel A, and those with substitutions at position 8-9 are shown in B. Shown are combined data (mean±S.E.M.) from 3 to 10 experiments, each performed in duplicate. Symbols are defined in the key.

Amino Acid Sequences: The amino acid sequences in this application use either the single letter or three letter designations for the amino acids. These designations are well known to one of skill in the art and can be found in numerous readily available references, such as for example in *Cooper, G. M., The Cell* 1997, ASM Press, Washington, D.C. or Ausubel et al., *Current Protocols in Molecular Biology,* 1994. Where substitutions in a sequence are referred to, for example, as Ser-3→Ala or [Ala$^3$]peptide, this means that the serine in the third position from the N-terminal end of the polypeptide is replaced with another amino acid, Alanine in this instance.

In the present application [M]PTH(1-14) is defined as [Ala$^{3,12}$,Gln$^{10}$,Har$^{11}$,Trp$^{14}$]PTH(1-14)amide. [M]PTH(1-21)is defined as [Ala$^{3,12}$,Nle$^8$,Gln$^{10}$,Har$^{11}$,Trp$^{14}$,Arg$^{19}$,Tyr$^{21}$]PTH(1-21)amide. [M]PTH(1-11) is defined as [Ala$^3$, Gln$^{10}$,Har$^{11}$]PTH(1-11)amide.

In the present application, "Aib" refers to α-aminoisobutyric acid; "Har" refers to homoarginine; "Nle" refers to norleucine; and other amino acids are in either the conventional one- or three-letter codes.

Biological Activity of the Protein: This expression refers to any biological activity of the polypeptide. Examples of these activities include, but are not limited to metabolic or physiologic function of compounds of SEQ ID NO: 1 or SEQ ID NO: 8 or derivatives thereof, including similar activities or improved activities, or those activities with decreased undesirable side-effects. Also included are antigenic and immunogenic activities of the above-described compounds.

Derivative or Functional Derivative: The term "derivative" or "functional derivative" is intended to include "variants," the "derivatives," or "chemical derivatives" of the PTH molecule. A "variant" of a molecule such as for example, a compound of SEQ ID NO: 1 or derivative thereof is meant to refer to a molecule substantially similar to either the entire molecule, or a fragment thereof. An "analog" of a molecule such as for example, a compound of SEQ ID NO: 1or derivative thereof is meant to refer to a non-natural molecule substantially similar to either the SEQ ID NO: 1 molecules or fragments thereof.

PTH derivatives contain changes in the polypeptide relative to the native PTH polypeptide of the same size. The sequence of the native PTH(1-14) polypeptide is the first fourteen amino acids of SEQ. ID NO: 17 (human PTH (1-21)) or SEQ. ID NO: 18(rat PTH(1-21)). A molecule is said to be "substantially similar" to another molecule if the sequence of amino acids in both molecules is substantially the same, and if both molecules possess a similar biological activity. Thus, two molecules that possess a similar activity, may be considered variants, derivatives, or analogs as that term is used herein even if one of the molecules contains additional amino acid residues not found in the other, or if the sequence of amino acid residues is not identical. PTH derivatives, however, need not have substantially similar biological activity to the native molecule. In some instances PTH derivatives have substantially different activity than the native PTH. For example, a derivative may be either an antagonist or an agonist of the PTH receptor.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Fragment: A "fragment" of a molecule such as for example, SEQ ID NO: 1 or derivative thereof is meant to refer to any polypeptide subset of these molecules.

Fusion protein: By the term "fusion protein" is intended a fused protein comprising compounds such as for example, SEQ ID NO: 1 or derivatives thereof, either with or without a "selective cleavage site" linked at its N-terminus, which is in turn linked to an additional amino acid leader polypeptide sequence.

Polypeptide: Polypeptide and peptide are used interchangeably. The term polypeptide refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids and include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translational modifications or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties,* 2nd Ed., T. E. Creighton, W. H. Freeman and Company, New York, 1993 and Wold, F., Posttranslational Protein Modifications: Perspectives and Prospects, pgs. 1-12 in *Posttranslational Covalent Modification of Proteins,* B. C. Johnson, Ed., Academic Press. New York, 1983; Seifter et al., "Analysis for protein modifications and nonprotein cofactors", *Methods in Enzymol.* 182:626-646 (1990) and Rattan et al., "Protein Synthesis: Posttranslational Modifications and Aging", *Ann NY Acad Sci* 663:48-62 (1992).

PTH Analogs—Structural and Functional Properties

α-aminoisobutyric acid (Aib) was introduced into short N-terminal PTH peptide analogs. The numerous NMR studies of PTH(1-34) analogs, performed in a variety of polar or non-polar solvents, have generally indicated two domains of secondary structure: a stable C-terminal helix extending approximately from Ser-17 to Val-31, and a shorter and less stable amino-terminal helix, extending variably from Ser-3 to Lys-13, the two domain being connected by a bend or turn region (Marx, U. C., et al., *Biochem. Biophys. Res. Commun.* 267:213-220 (2000); Chen, Z., et al., *Biochemistry* 39:12766-12777 (2000); Marx, U. C., et al., *J. Biol Chem.* 270:15194-15202 (1995); Marx, U. C., et al., *J. Biol. Chem.* 273:4308-4316 (1998); Pellegrini, M., et al., *Biochemistry* 37:12737-12743 (1998); Gronwald, W., et al., *Biol. Chem. Hoppe Seyler* 377:175-186 (1996); Barden, J. A., and Kemp, B. E., *Biochemistry* 32:7126-7132 (1993)). The recent crystallographic study of PTH(1-34) indicated a continuous α-helix extending from Ser-3 to His-32 and containing only a slight 15° bend at the midsection. However, NMR data indicates that the N-terminal α-helix is relatively weak. Helix-stabilizing modifications, such as the introduction of Aib residues, offer significant benefits in terms of peptide potency, and result in short peptides (≦14 amino acids) with activity comparable to PTH (1-34).

Described herein are novel "minimized" variants of PTH that are small enough to be deliverable by simple non-injection methods. The variants of the present invention contain substitutions in the first 14 amino acids of the polypeptide. The new polypeptides correspond to the 1-21, 1-20, 1-19, 1-18, 1-17, 1-16, 1-15, 1-14, 1-13, 1-12, 1-11, and 1-10 amino acid sequence of the mature PTH polypeptide. The shorter variants (≦PTH1-14) have a molecular weight of less than 2,000 daltons.

The primary amino acid sequence of the native human PTH(1-21) peptide (N-terminus to C-terminus) is SerValSerGluIleGlnLeuMetHisAsnLeuGlyLysHisLeuAsnSerMetGluArgVal (SEQ ID NO: 17), whereas the primary sequence of the native rat PTH (1-21) is AlaValSerGluIleGlnLeuMetHisAsnLeuGlyLysHisLeuAlaSerValGluArgMet (SEQ ID NO. 18).

As protein products, compounds described herein are amenable to production by the techniques of solution- or solid-phase peptide synthesis. The solid phase peptide synthesis technique, in particular, has been successfully applied in the production of human PTH and can be used for the production of these compounds (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991). The synthetic peptide synthesis approach generally entails the use of automated synthesizers and appropriate resin as solid phase, to which is attached the C-terminal amino acid of the desired compounds of SEQ ID NO: 1 or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of such as for example, SEQ ID NO: 1 and derivatives thereof which incorporate amino acids that are not genetically encoded, such as Aib.

In accordance with another aspect of the present invention, substituents are attached to the free amine of the N-terminal amino acid of compounds of the present invention standard methods known in the art. For example, alkyl groups, e.g., $C_{1-12}$ alkyl, are attached using reductive alkylation. Hydroxyalkyl groups, e.g. $C_{1-12}$ hydroxyalkyl, are also attached using reductive alkylation wherein the free hydroxy group is protected with a t-butyl ester. Acyl groups, e.g., $COE_1$, are attached by coupling the free acid, e.g., $E_1COOH$, to the free amino of the N-terminal amino acid. Additionally, possible chemical modifications of the C-terminal end of the polypeptide are encompassed within the scope of the invention. These modifications may modify binding affinity to the receptor.

Also contemplated within the scope of this invention are those compounds such as for example, SEQ ID NO: 1 and derivatives thereof with altered secondary or tertiary structure, and/or altered stability, which still retain biological activity. Such derivatives might be achieved through lactam cyclization, disulfide bonds, or other means known to a person of ordinary skill in the art.

Utility and Administration of Compounds of the Invention

Compounds of the invention or derivatives thereof have multiple uses. These include, inter alia, agonists or antagonists of the PTH receptor, prevention and treatment of a variety of mammalian conditions manifested by loss of bone mass, diagnostic probes, antigens to prepare antibodies for use as diagnostic probes and even as molecular weight markers. Being able to specifically substitute one or more amino acids in the PTH polypeptide permits construction of specific molecular weight polypeptides.

In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are also indicated for the prophylaxis and therapeutic treatment of hypoparathyroidism. Finally, the compounds of this invention are indicated for use as agonists for fracture repair and as antagonists for hypercalcemia.

In general, compounds of the present invention, or salts thereof, are administered in amounts between about 0.01 and 1 µg/kg body weight per day, preferably from about 0.07 to about 0.2 µg/kg body weight per day. For a 50 kg human female subject, the daily dose of biologically active compound is from about 0.5 to about 50 µgs, preferably from about 3.5 to about 10 µgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation.

The selection of the exact dose and composition and the most appropriate delivery regimen will be influenced by, inter alia, the pharmacological properties of the selected compounds of the invention, the nature and severity of the condition being treated, and the physical condition and mental acuity of the recipient.

Representative preferred delivery regimens include, without limitation, oral, parenteral, subcutaneous, transcutaneous, intramuscular and intravenous, rectal, buccal (including sublingual), transdermal, and intranasal insufflation.

Pharmaceutically acceptable salts retain the desired biological activity of the compounds of the invention without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like. Pharmaceutically acceptable buffers include but are not limited to saline or phosphate buffered saline. Also included in these solutions may be acceptable preservative known to those of skill in the art.

A further aspect of the present invention relates to pharmaceutical compositions comprising as an active ingredient compounds of the invention or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acyl-carnitines. Formulations for nasal administration may be solid and may contain excipients for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for the most preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly(lactic/glycolic) acid, as described in the pioneering work of Kent, Lewis, Sanders, and Tice, U.S. Pat. No. 4,675,189. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987.

Like PTH, the PTH variants may be administered in combination with other agents usefull in treating a given clinical condition. When treating osteoporosis and other bone-related disorders for example, the PTH variants may be administered in conjunction with a dietary calcium supplement or with a vitamin D analog (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

PTH Analog Receptor-Signaling Activities

A crucial step in the expression of hormonal action is the interaction of hormones with receptors on the plasma membrane surface of target cells. The formation of hormone-receptor complexes allows the transduction of extracellular signals into the cell to elicit a variety of biological responses.

Polypeptides described herein can be screened for their agonistic or antagonistic properties using the cAMP accumulation assay. Cells expressing PTH-1 receptor on the cell surface are incubated with native PTH(1-84) for 5-60 minutes at 37° C., in the presence of 2 mM IBMX (3-isobutyl-1-methyl-xanthine, Sigma, St. Louis, Mo.). Cyclic AMP accumulation is measured by specific radio-immunoassay. A compound that competes with native PTH(1-84) or PTH(1-34) for binding to the PTH-1 receptor, and that inhibits the effect of native PTH(1-84) or PTH(1-34) on cAMP accumulation, is considered a competitive antagonist. Such a compound would be useful for treating hypercalcemia.

Conversely, a PTH analog described herein or a derivative thereof that does not compete with native PTH(1-84) or PTH(1-34) for binding to the PTH-1receptor, but which still prevents native PTH(1-84) or PTH(1-34) activation of cAMP accumulation (presumably by blocking the receptor activation site) is considered a non-competitive antagonist. Such a compound would be useful for treating hypercalcemia.

The compounds described herein that compete with native PTH(1-84) or PTH(1-34)) for binding to the PTH-1 receptor, and which stimulates cAMP accumulation in the presence or absence of native PTH(1-84) or PTH(1-34) are competitive agonists. A compound that does not compete with native PTH(1-84) or PTH(1-34) for binding to the PTH-1 receptor but which is still capable of stimulating cAMP accumulation in the presence or absence of native PTH(1-84) or PTH(1-34), or which stimulates a higher cAMP accumulation than that observed by a compound of the invention or a derivative thereof alone, would be considered a non-competitive agonist.

Therapeutic Uses of PTH Analogs

Some forms of hypercalcemia and hypocalcemia are related to the interaction between PTH and PTHrP and the PTH-1 and receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypernephroma. Hypocalcemia, a condition in which the serum calcium level is abnormally low, may result from a deficiency of effective PTH, e.g., following thyroid surgery.

By "agonist" is intended a ligand capable of enhancing or potentiating a cellular response mediated by the PTH-1 receptor. By "antagonist" is intended a ligand capable of inhibiting a cellular response mediated by the PTH-1 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient therapeutically effective amount of a compound of the invention or a derivative thereof sufficient to inhibit activation of the PTH-1 receptor of said patient.

In this embodiment, a patient who is suspected of having a disorder resulting from altered action of the PTH-1 receptor can be treated using compounds of the invention or derivatives thereof of the invention which are a selective antagonists of the PTH-1 receptor. Such antagonists include compounds of the invention or derivatives thereof of the invention which have been determined (by the assays described herein) to interfere with PTH-1 receptor-mediated cell activation or other derivatives having similar properties.

To administer the antagonist, the appropriate compound of the invention or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of a compound of the invention or a derivative thereof binding to the PTH-1 receptor. Typical dosage would be 1 ng to 10 mg of the peptide per kg body weight per day.

In accordance with yet a further aspect of the invention, there is provided a method for treating osteoporosis, comprising administering to a patient a therapeutically effective amount of a compound of the invention or a derivative thereof, sufficient to activate the PTH-1 receptor of said patient. Similar dosages and administration as described above for the PTI/PTHrP antagonist, can be used for administration of a PTH/PTHrP agonist, e.g., for treatment of conditions such as osteoporosis, other metabolic bone disorders, and hypoparathyroidism and related disorders.

It will be appreciated to those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to be limiting of the invention, unless herein specified.

EXAMPLES

The following protocols and experimental details are referenced in the examples that follow.

Peptides. Each peptide utilized in this study contained a free amino acid terminus and a carboxamide at the C-terminus. Peptides were prepared on automated peptide synthesizers (model 430A PE, Applied Biosystems, Foster City, Calif., or Model 396 MBS Advanced Chem Tect, Louisville, Ky.) using Fmoc main-chain protecting group chemistry, HBTU/HOBt/DIEA (1:1:2 molar ratio) for coupling reactions, and TFA-mediated cleavage/sidechain-deprotection (MGH Biopolymer Synthesis Facility, Boston, Mass.). All peptides were desalted by adsorption on a C18-containing cartridge, and purified further by HPLC. The dry peptide powders were reconstituted in 10 mM acetic acid and stored at −80° C. The purity, identity, and stock concentration for each peptide was secured by analytical HPLC, Matrix-assisted laser desorption/ionization (MALDI) mass spectrometry and amino acid analysis. Radiolabeling of [M]PTH(1-21) and [Aib$^{1,3}$,M]PTH(1-21) was performed using $^{125}$I-Na (2,200 Ci/mmol, NEN) and chloramine-T; the resultant radioligands were purified by HPLC.

Cell Culture. The cell line HKRK-B28 (Takasu, H., et al., *J. Bone Miner. Res.* 14:11-20 (1999)) was derived from the porcine kidney cell line, LLC-PK$_1$ by stable transfection with plasmid DNA encoding the human P1R and expresses ~280,000 receptors per cell. These cells, as well as COS-7 cells and SaOS-2-B10 cells, were cultured at 27° C. in T-75 flasks (75 mm$^2$) in Dulbecco's modified Eagle's medium (DMEM) supplemented with fetal bovine serum (10%), penicillin G (20 units/ml), streptomycin sulfate (20 μg/ml) and amphotericin B (0.05 μg/ml) in a humidified atmosphere containing 5% $CO_2$. Stock solutions of EGTA/trypsin and antibiotics were from GIBCO; fetal bovine serum was from Hyclone Laboratories (Logan, Utah). COS-7 cells sub-cultured in 24-well plates were transfected with plasmid DNA (200 ng per well) encoding the wild-type human P1R or truncated human P1R deleted for residues (24-181) (Shimizu, M., et al., J. Biol. Chem. 275:21836-21843 (2000)) that was purified by cesium chloride/ethidium bromide density gradient centrifugation, and FuGENE 6 transfection reagent (Roche Indianapolis Ind.) according to the manufacturer's recommended procedure. All cells, in 24-well plates, were treated with fresh media and shifted to 33° C. for 12 to 24 h prior to assay.

cAMP Stimulation. Stimulation of cells with peptide analogs was performed in 24-well plates. Cells were rinsed with 0.5 mL of binding buffer (50 mM Tris-HCl, 100 nM NaCl, 5 mM KCl, 2 mM $CaCl_2$, 5% heat-inactivated horse serum, 0.5% fetal bovine serum, adjusted to pH 7.5 with HCl) and treated with 200 μL of cAMP assay buffer (Delbecco's modified Eagle's medium containing 2 mM 3-isobutyl-1-methylxanthine, 1 mg/mL bovine serum albumin, 35 mM Hepes-NaOH, pH 7.4) and 100 μL of binding buffer containing varying amounts of peptide analog (final volume=300 μL). The medium was removed after incubation for 30 to 60 minutes at room temperature, and the cells were frozen on dry ice, lysed with 0.5 mL 50 mM HCl, and refrozen (~80° C). The cAMP content of the diluted lysate was determined by radioimmunoassay. The $EC_{50}$ response values were calculated using nonlinear regression (see below).

Competition Binding. Binding reactions were performed with HKRK-B28 cells or in COS-7 cells in 24-well plates. The cells were rinsed with 0.5 mL of binding buffer, and then treated successively with 100 μL binding buffer, 100 μL of binding buffer containing various amounts of unlabeled competitor ligand, and 100 μL of binding buffer containing ca. 100,000 cpm of $^{125}$I-[M]PTH(1-21) or $^{125}$I-[Aib$^{1,3}$,M]PTH (1-21)} (ca. 26 fmol; final volume=300 μL). Incubations were 4 to 6 h at 4° C., at which time near equilibrium conditions were attained. Cells were then placed on ice, the binding medium was removed, and the monolayer was rinsed three times with 0.5 mL of cold binding buffer. The cells were subsequently lysed with 0.5 mL 5N NaOH and counted for radioactivity. For each tracer and in each experiment, the non-specific binding was determined as the radioactivity that bound in the presence of the same unlabeled peptide at a concentration of 1 μM, and was ~1% of total radioactivity added for each tracer. The maximum specific binding ($B_0$) was the total radioactivity bound in the absence of competing ligand, corrected for nonspecific binding, and for each tracer, ranged from 8% to 20% of the total radioactivity added. Nonlinear regression was used to calculate binding $IC_{50}$ values (see below). Scatchard transformations of homologous competition binding data derived from studies with 26 fmol of $^{125}$I-[Aib$^{1,3}$,M]PTH(1-21) were employed for estimations of apparent equilibrium dissociation constant ($k_{Dapp}$s) and total number of ligand binding sites ($B_{max}$), assuming a single class of binding sites and equal affinities of the iodinated and non iodinated ligand.

Stimulation of Inositol Phosphate Production. COS-7 cells transfected as above with P1R-WT were treated with serum-free, inositol-free DMEM containing 0.1% bovine serum albumin and [$^3$H]myo-inositol (NEN, Boston, Mass.) (2 μCi/mL) for 16 h prior to assay. At the time of the assay, the cells were rinsed with binding buffer containing LiCl (30 mM) and treated with the same buffer with or without a PTH analog. The cells were then incubated at 37° C. for 40 min, after which the buffer was removed and replaced by 0.5 mL of ice cold 5% trichloroacetic acid solution. After 3 h on ice, the lysate was collected and extracted twice with ethyl ether. The lysate was then applied to an ion exchange column (0.5 mL resin bed) and the total inositol phosphates were eluted as described previously (Berridge, M. J., et al., Biochem. J. 212:473-482 (1983)), and counted in liquid scintillation cocktail.

Inhibition of Chondrocyte Differentiation in Embryonic Mouse Metatarsals. Metatarsals from embryonic day (E) 15.5 mouse embryos were excised and cultured in a 37° C. humidified incubator (5% $CO_2$) in serum -free αXMEM media in 24 well plates. Sixteen hours later, a PTH analog or vehicle was added, and the samples were incubated for an additional 48 h in 37° C. with peptide or vehicle added again at the 24 h time point. At the end of the 64 h incubation period, the samples were fixed with 10% formalin/phosphate-buffered saline, then directly visualized on a dissecting microscope using white light. Sections were processed for in-situ hybridization analysis using $^{35}$S-labeled riboprobes specific for collagen type X mRNA, a developmental marker gene expressed only in hypertrophic chrondrocytes of the growth plate.

Circular Dichroism. Circular Dichroism spectra were recorded on a Jasco model 710 spectropolarimeter; peptides were analyzed at a concentration of 20 μM in 50 mM sodium phosphate buffer pH 7.4, or the same buffer containing 2,2, 2-trifluoroethanol at 20% (v/v). Spectroscopic scans were preformed at 20° C. and at wavelengths between 185 and 255 nM, with data recored at each 1 nM interval. The spectral bandwidth was 1.5 nM and 8 scans were accumulated and averaged for each sample. At each wavelength, the mean residue elipticity [θ×100/l×C×n); where θ is the raw elipticity value (in dimensions of millidegree), l is the sample path length, C=is the molar peptide concentration, and n is the number of residues in the peptide (Bowen, W. P., and Jerman, J. C., Trends in Pharmacol. Sci. 16: 413-417 (1995)). The helical content of each peptide was estimated by dividing [θ] observed at 222 nM for that peptide by −28,100, which is the reported $[\theta]_{222}$obs for a model helical decapeptide (Bowen, W. P., and Jerman, J. C., Trends in Pharmacol. Sci. 16: 413-417 (1995)).

Data Calculation. Calculations were performed using Microsoft® Excel. Nonlinear regression analyses of binding and cAMP dose-response data were performed using the four-parameter equation: $y_p$=Min+[(Max−Min)/(1+ $(IC_{50}/x)^{slope}$)]. The Excel Solver function was utilized for parameter optimization, as described previously (Carter, P. H., et al., Endocrinology 140: 4972-4981 (1999); Bowen, W. P., and Jerman, J. C., Trends in Pharmacol. Sci. 16: 413-417 (1995)). Differences between paired data sets were statistically evaluated using a one-tailed Student's t-test, assuming unequal variances for the two sets.

Example 1

Aib-scan in [M]PTH(1-14)

The effect of introducing individual Aib substitutions at each position in the scaffold peptide [M]PTH(1-14) (Shimizu, M., et al., Endocrinology (2001) (In Press))) were analyzed. In cAMP stimulation assays in HKRK-B28 cells, the parent peptide [M]PTH(1-14) stimulated approximately the same (~70-fold) maximun (Emax) increase in intracellular cAMP that was induced by PTH(1-34), but the potency ($EC_{50}$) of the shorter peptide was 40-fold less than that of PTH(1-34) ($EC_{50}$ s=100±20 and 2.5±0.4. nM, respectively) (FIG. 1 and Table 1). Most of the Aib substitutions diminished potency. Severe reductions occured with Aib substitutions at positions 6, 8 and 9 (all>2,300-fold), moderate reductions occurred with substitution at positions 2, 4, 5 and 11 (all 170 to 670-fold) and minor reductions occurred with substitutions at positions 7, 10, 12, 13 and 14 (all<3-fold; Table 1). Substitution of Aib at positions 1 and 3 resulted in peptides with 10- and 8-fold improvements in potency, relative to [M]PTH (1-14), respectively (P≦0.01). These Aib-scan data extend previous alanine-scan and substitution analyses of PTH(1-14) analogs, in which residues in the (1-9) region, excluding residue 3, were found to be intolerant to substitution, and residues 3 and 10-14. were found to be relatively tolerant (Luck, M. D., et al., *Molecular Endocrinology* 13:670-680 (1999); Shimizu, M., et al., *J. Biol. Chem.* 275:19456-19460 (2000); Pellegrini, M., et al., *J. Biol. Chem.* 273:10420-10427 (1998)).

The P1R-binding properties of these analogs were assayed in competition studies performed in HKRK-B8 cells. In previous studies, PTH(1-14) binding could not be detected using $^{125}$I-PTH(1-34) and related N-terminally intact and relatively unmodified radioligands (Luck, M. D., et al., *Molecular Endocrinology* 13:670-680 (1999)). However, measurable PTH(1-14) binding was observed with $^{125}$I-PTH(3-34) used as a tracer radioligand (Hoare, S. R. J., et al., *J. Biol. Chem* 276:7741-7753 (2001); Shimizu, M., et al., *Endocrinology* (2001) (In Press)). Receptor binding affinity was assessed using a tracer radioligand that was structurally more homologous to the [M]PTH(1-14) analogs being investigated. The radiolabeled peptide $^{125}$I-[Ala$^{3,12}$Nle$^8$Gln$^{10}$,Har$^{11}$,Trp$^{14}$, Tyr$^{15}$]PTH(1-15)amide was evaluated, but did not bind detectably to HKRK-B28 cells. A similar analog, which was extended to position 21 and contained the affinity-enhancing substitution of Glu$^{19}$→Arg (Takasu, H., et al., *Biochemistry* 38:13453-13460 (1999); Kronenberg, H. M., et al., *Recent Prog. Horm. Res.* 53:283-301 (1998)), was prepared. The resulting radioligand $^{125}$I-[M]PTH(1-21) bound adequately to the P1R expressed intact HKRK-B28 cells, as the amount of specifically bound radioactivity (e.g. that which could be inhibited by excess unlabeled [M]PTH(1-2) peptide), was ~15% to 20% of total radioactivity added, and that which bound to untransfected LLC-PK1 cells was<2% of total added. Thus, this tracer ligand was suitable for competition analyses.

The binding of $^{125}$I-[M]PTH(1-21) to HKRK-B28 cells was fully inhibited by PTH(1-34) (IC$_{50}$=18±3 nM) and more weakly but to near completion by [M]PTH(1-14) (IC$_{50}$=13,000±3,000 nM, Table 1). Relative to the apparent binding affinity of [M]PTH(1-14), most of the Aib substitutions reduced affinity, in accordance with the corresponding effects on cAMP-signaling potency (Table 1). The only Aib substitutions that improved affinity significantly were those at positions 1 and 3 (13- and 8-fold, respectively, Aib at position 10 showed a trend towards causing a 1.4-fold improvement in affinity, P=0.16). Strong (>10-fold) reductions in affinity occurred with Aib substitutions at positions 4, 7, 8 and 9, while mild (<10-fold) reductions occurred with the Aib at positions 2, 5, 12, 13 and 14. While most of the Aib substitutions had effects on receptor -binding affinity that were approximately proportional to their effects on cAMP-stimulating potency, those at positions 2 and 6 had less of an effect on binding than on potency. Thus, these two substitutions reduced affinity ~3-fold, relative to [M]PTH(1-14), while they reduced potency ~470- and ~2,300-fold, respectively (Table 1).

Figure 2:
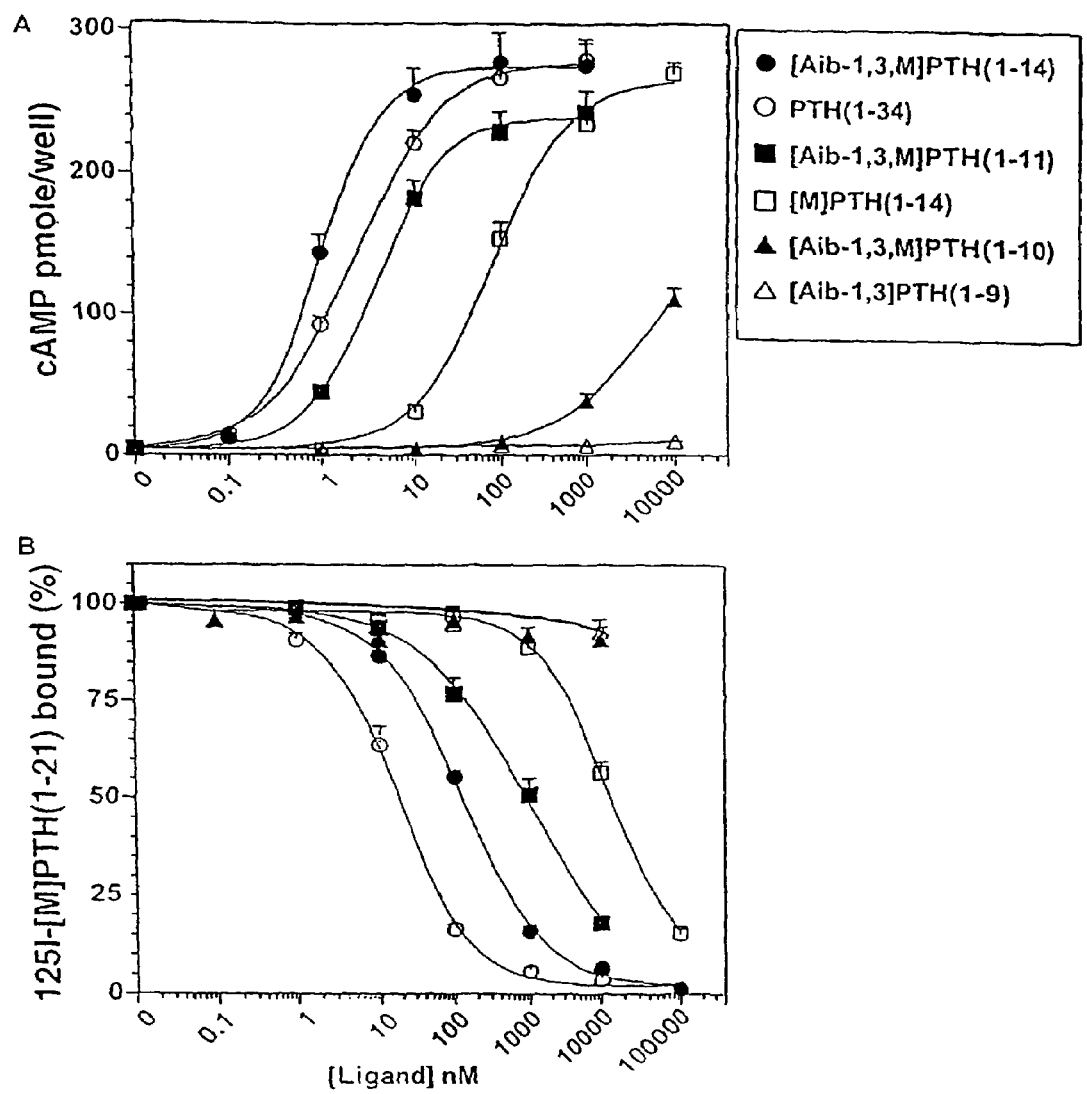
FIG. 2. cAMP-signaling and binding properties of PTH analogs in HKRK-B28 cells. Peptides were evaluated in HKRK-B28 cells for the capacity to stimulate intracellular cAMP accumulation (A) and the capacity to inhibit binding of $^{125}$I-[M]PTH(1-21) (B). Shown are combined data (mean±S.E.M.) from 3 or 4 experiments, each performed in duplicate. Peptides and corresponding symbols are identified in the key.

Combining the Aib substitutions at positions 1 and 3 revealed an additive effects, as [Aib$^{1,3}$,M]PTH(1-14) was 90-fold more potent in stimulating cAMP formation than was [M]PTH(1-14) (EC$_{50}$ s=1.1±0.1 nM, 100±20 nM, respectively), and at least as potent as PTH(1-34) (EC$_{50}$=2.5±0.4 nM, P=0.01, FIG. 2A and Tale 1). The effects of the single Aib substitutions at position 1 and 3 on receptor-binding affinity were also additive, as [Aib$^{1,3}$,M]PTH(1-14) bound with 100-fold higher apparent affinity than did [M]PTH(1-14) (FIG. 2B and Table 1). Aib substitutions were subsequently introduced at positions 1 and 3 in [M]PTH(1-11) analog to determine if the paired substitution could enhance activity of the shorter peptide sequence. Previously, it was shown that while native PTH peptides shorter than (1-14) were devoid of cAMP-stimulating activity (Luck, M. D., et al., *Molecular Endocrinology* 13:670-680 (1999)), modified PTH(1-11) analogs, such as [M]PTH(1-11) could induce a full cAMP response in HKRK-B28 cells, albeit with a potency (EC$_{50}$=3 μM) nearly 1,000-fold weaker than that of PTH(1-34) (Shimizu, M., et al., *Endocrinology* (2001) (In Press)). In cAMP stimulation assays in HKRK-B28 cells, [Aib$^{1,3}$,M]PTH(1-11) was fully efficacious and its potency (EC$_{50}$ 4.0±0.8 nM) was 1,000-fold greater than that of [M]PTH(1-11) (Shimizu, M., et al., *Endocrinology* (2001) (In Press)) and nearly equal to that of PTH (1-34) (FIG. 2A, Table 1). The Aib-1,3 modification also enhanced potency of PTH(1-10) analog, as [Aib$^{1,3}$,Gln$^{10}$]PTH(1-10) was 50-fold more potent than our previously most potent PTH(1-10) analog, [Ala$^3$,Gln$^{10}$]PTH(1-10) (EC$_{50}$ s=16±2 μM and ~800 μM, respectively) (Shimizu, M., et al., *Endocrinology* (2001) (In Press)) (FIG. 2A, Table 1). The 4000-fold weaker potency that [Aib$^{1,3}$,Gln$^{10}$]PTH(1-10) exhibited, relative to that of [Aib$^{1,3}$,M]PTH(1-1 1), indicated the importance of the position 11 residue (homoarginine) in the activities of the Aib-containing pep tides. Little or no stimulation of cAMP accumulation was observed with [Aib$^{1,3}$]PTH(1-9) (FIG. 2A and Table 1). In competition binding assays, [Aib$^{1,3}$,M]PTH(1-11) effectively inhibited $^{125}$I-[Aib$^{1,3}$,M[PTH(1-21) binding to HKRK-B8 cells (IC$_{50}$=970±300 nM), but [Aib$^{1,3}$,Gln$^{10}$]PTH(1-10) and [Aib$^{1,3}$]PTH(1-9) did not bind detachably (FIG. 2B and Table 1).

TABLE 1 cAMP Stimulation and hP1R-Binding Properties in HKRK-B28 cells

| # Peptide | cAMP | | | Binding | |
|---|---|---|---|---|---|
| | EC$_{50}$ nM | EMax$_{(obs.)}$ pmole/well | (n) | IC$_{50}$ nM | (n) |
| 92 PTH(1-34) | 2.5 ± 0.4 | 280 ± 11 | 10 | 18 ± 3 | 7 |
| 621 [M]PTH(1-14) | 100 ± 20 | 270 ± 8 | 10 | 13,000 ± 3,000 | 4 |

TABLE 1-continued cAMP Stimulation and hP1R-Binding Properties in HKRK-B28 cells

| # Peptide | cAMP EC$_{50}$ nM | EMax$_{(obs.)}$ pmole/well | (n) | Binding IC$_{50}$ nM | (n) |
|---|---|---|---|---|---|
| Aib scan in [M]PTH(1-14) | | | | | |
| 622 Aib-1 | 10 ± 3 | 273 ± 6 | 6 | 980 ± 160 | 3 |
| 623 Aib-2 | 47,000 ± 13,000 | 168 ± 6 | 3 | 50,000 ± 11,000 | 3 |
| 624 Aib-3 | 13 ± 3 | 269 ± 7 | 6 | 1,700 ± 200 | 3 |
| 625 Aib-4 | 17,000 ± 3,400 | 221 ± 10 | 3 | 148,000 ± 40,000 | 3 |
| 626 Aib-5 | 66,000 ± 38,000 | 169 ± 18 | 3 | N.B. | 3 |
| 627 Aib-6 | 230,000 ± 78,000 | 116 ± 12 | 3 | 31,000 ± 7,000 | 3 |
| 628 Aib-7 | 2,600 ± 980 | 275 ± 8 | 3 | 490,000 ± 170,000 | 3 |
| 629 Aib-8 | 1,500,000 ± 970,000 | 34 ± 7 | 3 | N.B. | 3 |
| 630 Aib-9 | 710,000 ± 330,000 | 51 ± 8 | 4 | N.B. | 3 |
| 631 Aib-10 | 3,000 ± 2,100 | 214 ± 22 | 3 | 9,100 ± 1,500 | 3 |
| 632 Aib-11 | 67,000 ± 51,000 | 96 ± 18 | 4 | N.B. | 3 |
| 633 Aib-12 | 440 ± 300 | 263 ± 9 | 3 | 15,000 ± 3,000 | 3 |
| 634 Aib-13 | 480 ± 250 | 259 ± 10 | 4 | 44,000 ± 8,000 | 3 |
| 635 Aib-14 | 350 ± 100 | 273 ± 6 | 3 | 79,000 ± 27,000 | 3 |
| Aib-1,3 in [M]PTH(1-X) | | | | | |
| 608 [M]PTH(1-21) | N.D. | | | 53 ± 4 | 3 |
| 674 [Aib$^{1,3}$, M]PTH (1-21) | 4.3 ± 1.6 | 284 ± 76 | 3 | 31 ± 7 | 3 |
| 671 [Aib$^{1,3}$, M]PTH (1-14) | 1.1 ± 0.1 | 278 ± 20 | 5 | 130 ± 20 | 5 |
| 682 [Aib$^{1,3}$, M]PTH (1-11) | 4.0 ± 0.8 | 243 ± 15 | 4 | 970 ± 300 | 3 |
| 684 [Aib$^{1,3}$, M]PTH (1-10) | 16,000 ± 2,000 | 111 ± 8 | 4 | N.B. | 3 |
| 696 [Aib$^{1,3}$]PTH (1-9) | >10,000 | 10 ± 1 | 3 | N.B. | 3 |

Peptides PTH(1-34) ([Nle$^{8,21}$, Tyr$^{34}$]PTH(1-34)amide), [M]PTH(1-14) (M = Ala$^{3,12}$, Gln$^{10}$, Har$^{11}$, Trp$^{14}$), and [M]PTH(1-14 analogs, or C-terminally truncated derivatives thereof, containing α-aminoisobutyric acid (Aib) substitutions at the indicated positions were functionally evaluated in HKRK-B28 cells.
"M" in [Aib$^{1,3}$, M]PTH(1-21) = Nle$^8$, Gln$^{10}$, Har$^{11}$, Ala$^{12}$, Trp$^{14}$, Arg$^{19}$ and Tyr$^{21}$.
The basal cAMP values (not subtracted) were 4.0 ± 0.1 pmole/well (n = 10). Peptides were based on the rat PTH sequence and were carboxy-amidated. Competition binding analyses were performed with $^{125}$I-[M]PTH(1-21)amide (Ala$^{1,3}$) as tracer for 4 h at 4° C. Data are means (± S.E.M.) Of the number of experiments indiated (n).
N.B., no binding was detected at a peptide concentration of 10 μm; N.D.; the experiment was not done.
The sequence of MPTH(1-14) is: Ala-Val-Ala*-Glu-Ile-Gln-Leu-Met-His-Gln*-Har*-Ala*-Lys-Trp* where the asterisk denotes substituted amino acids are not found at that position in native rat PTH(1-14).

Example 2

Analog Activity in COS-7 Cells

Figure 3:
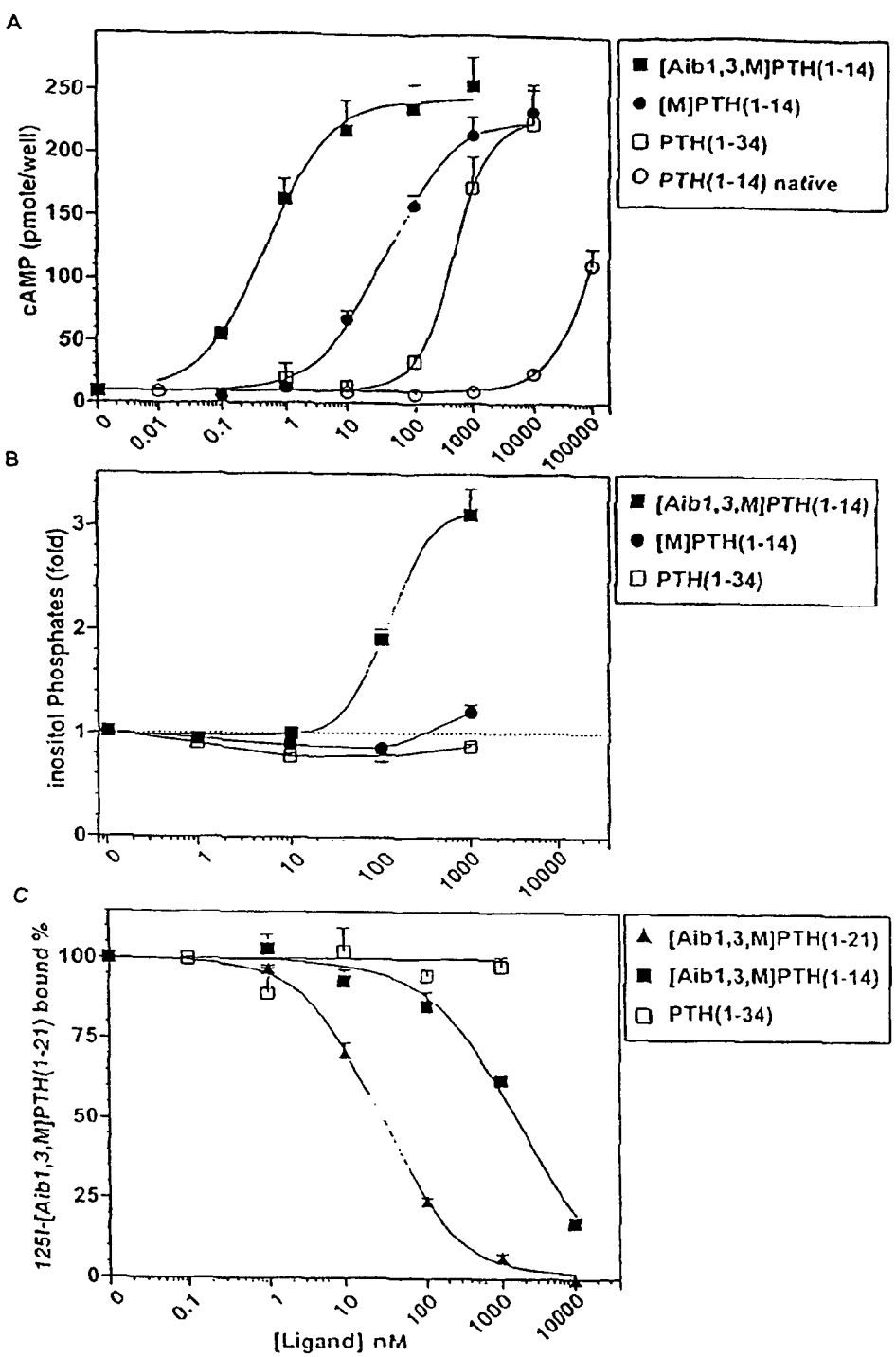
FIG. 3. Signaling and binding properties of PTH analogs in COS-7 cells expressing an N-terminally truncated P1R. COS-7 cells were transiently transfectd with P1R-delNt, a truncated P1R which is deleted for most of the amino-terminal extracellular domain, and subsequently used to evaluate the capacities of the indicated PTH analogs to stimulate intracellular cAMP accumulation (A); stimulate formation of $^3$H-inositol phosphates (IP$^1$+IP$^2$+IP$^3$) (B); and inhibit the binding of $^{125}$I-[Aib$^{1,3}$,M]PTH(1-21) (C). Each curve shows data combined (mean±S.E.M.) from 3 to 6 experiments, each performed in duplicate. The mean basal level of $^3$H-inositol phosphates (2,929±877 cpm/well) is indicated by the dashed iine. Peptides and corresponding symbols are identified in the key.

The possibility that the activity-enhancing effects of the Aib substitutions at positions 1 and 3 were mediated through the juxtamembrane (J) region of the receptor was investigated in COS-7 cells transiently transfected with P1R-delNt. P1R-delNt was a truncated P1R that lacked most of the amino-terminal extracellular domain. With this receptor construct, PTH(1-34) was a much weaker agonist than it was with P1R-WT, while other PTH(1-14) analogs exhibited approximately the same potency with P1R-delNt as with P1R-WT (Kaul, R., and Balaram, P., Bioorganic & Medicinal Chemistry 7:105-117 (1999)). Consistent with this, the cAMP-stimulating potency of [Aib$^{1,3}$,M]PTH(1-14) on P1R-delNt (EC$_{50}$=0.73±0.16 nM) was comparable to its potency on COS-7 cells expressing P1R-WT (1.2±0.6 nM) (Table 2). On P1R-delNt, [Aib$^{1,3}$,M]PTH(1-14) was 55-fold more potent than was [M]PTH(1-14) (EC$_{50}$=40±2 nM, FIG. 3A and Table 2). This result indicated that the potency-enhancing effects of the Aib-1,3 substitutions were exerted through the J domain of the receptor. Remarkably, [Aib$^{1,3}$,M]PTH(1-14) was as potent on P1R-delNt as PTH(1-34) was on P1R-WT (EC$_{50}$s=0.73±0.16 nM and 1.4±0.7 nM, respectively, P=0.4, Table 2) and the EMax induced by [Aib$^{1,3}$,M]PTH(1-14) on P1R-delNt was equal to that induced by PTH(1-34) on P1R-WT (250±20 picomole/well and 240±50 picomole/well, respectively, P=0.7, Table 2). As expected, PTH(1-34), was ~500-fold weaker on P1R-delNt than P1R -WT (EC$_{50}$s=680±110 nM and 1.4±0.7 nM, respectively; FIG. 3A and Table 2).

Heretofore, it was not possible to demonstrate a PLC response for any PTH analog in cells expressing P1R-delNt, including [M]PTH(1-14). The analog [Aib$^{1,33}$,M]PTH(1-14), however, induced an approximate 3-fold increase in inositol phosphate (IP) production, relative to the basal level of IPs, in COS-7 cells expressing P1R-delNt, while, as expected, PTH(1-34) and [M]PTH(1-14) were inactive (FIG. 3B). Thus, the truncated receptor can couple to the PCL signaling pathway when stimulated with the Aib-containing PTH peptide. With P1R-WT, both [Aib$^{1,3}$,M]PTH(1-14) and [M]PTH(1-14) stimulated the same 4-fold increase in IP formation that was observed for PTH(1-34) acting on this receptor, and with this receptor, [Aib$^{1,3}$,M]PTH(1-14) was 66-fold more potent than [M]PTH(1-14) (EC$_{50}$=71±9 nM, and 4,700±2,000 nM, respectively, Table 2). Thus, the Aib-1,3 substitutions enhance the ligand's capacity to stimulate PLC activity with P1R-WT, as well as with P1R-delNt.

The radioligand used in the above binding studies HKRK-B8 cells, $^{125}$I-[M]PTH(1-21), did not bind detectably to P1R-delNt. To potentially improve affinity of this peptide, the paired Aib-1,3 modifications were introduced to produce [Aib$^{1,3}$,M]PTH(1-21). The corresponding radioiodinated peptide, $^{125}$I-[Aib$^{1,3}$,M]PTH(1-21), bound to COS-7 cells expressing P1R-WT; thus, the specific binding of this tracer (e.g. that which could be inhibited by excess unlabeled [Aib$^{1,}$ $_3$,M]PTH(1-21) peptide) was ~10% and ~15% of the total radioactivity added, for each receptor, respectively. The total specific binding observed in COS-7 cells tranfected with vector DNA alone was <2% of total radioactivity added. This radioligand, therefore, enabled competition binding experiments to be performed with both the wild-type and truncated PTH-1 receptors. Scatchard transformation of homologous competition binding data obtained with $^{125}$I-[Aib$^{1,3}$, M]PTH (1-21) as tracer radioligand and varying amounts of unlabeled [Aib$^{1,3}$,M]PTH(1-21) indicated that the ligand's affinity at P1R-delNt was slightly (<2-fold) weaker than it was at P1R-WT ($K_{Dapp}$s=29±3 and 17±2 nM, respectively, P=0.01), while the corresponding $B_{max}$ values for the two receptors were not significantly different (1.3±0.1×10$^6$ receptors/cell and 1.9±0.8×10$^6$ receptors/cell respectively, P=0.3).

At the truncated receptor, [Aib$^{1,3}$,M]PTH(1-14), in addition to [Aib$^{1,3}$,M]PTH(1-21), effectively inhibited the binding of $^{125}$I-[Aib$^{1,3}$,M]PTH(1-21), whereas, PTH(1-34) did not (FIG. 3C). Like [Aib$^{1,3}$,M]PTH(1-21), the apparent binding affinities that [Aib$^{1,3}$,M]PTH(1-14) and [M]PTH(1-14) exhibited at P1R-delNt were comparable to the corresponding affinities observed at the wild-type P1R (Table 2). At both P1R-delNt and P1R-WT, the binding affinities of [Aib$^{1,3}$,M] PTH(1-14) were ~10-fold stronger than the corresponding affinities observed for [M]PTH(1-14). The Aib substitutions therefore enhanced the ligand's binding affinity for the J domain of the P1R.

TABLE 2

Functional properties of PTH analogs in COS-7 cells

| Peptide$^a$ | cAMP | | | PLC | | | Binding | |
|---|---|---|---|---|---|---|---|---|
| | EC$_{50}$ nM | EMAX$_{(obs.)}$ pmole/well | (n) | EC$_{50}$ nM | EMAX$_{(obs.)}$ foldxbasal | (n) | IC$_{50}$ nM | (n) |
| hP1R-WT | | | | | | | | |
| 92.5 PTH(1-34) | 1.4 ± 0.7 | 240 ± 50 | 3 | 17 ± 2 | 4.2 ± 0.6 | 3 | 12 ± 3 | 4 |
| 521 PTH(1-14) | 90,000 ± 34,000 | 140 ± 30* | 3 | — | | | N.B. | 3 |
| 621 [M]PTH(1-14) | 49 ± 21 | 240 ± 50 | 3 | 4,700 ± 2,000 | 3.9 ± 0.5 | 3 | 20,000 ± 3,000 | 3 |
| 674 [Aib$^{1,3}$M]PTH(1-21) | 0.8 ± 0.1 | 300 ± 30 | 3 | N.D. | | | 28 ± 5 | 6 |
| 671 [Aib$^{1,3}$M]PTH(1-14) | 1.2 ± 0.6 | 240 ± 40 | 3 | 71 ± 9 | 4.3 ± 0.6 | 3 | 2,250 ± 1,100 | 4 |
| 682 [Aib$^{1,3}$M]PTH(1-11) | 2.1 ± 0.7 | 190 ± 40 | 3 | N.D. | | | 16,000 ± 1,000 | 3 |
| 684 [Aib$^{1,3}$M]PTH(1-10) | 100,000 ± 40,000 | 120 ± 10* | 3 | N.D. | | | N.B. | 3 |
| hP1R-delNT | | | | | | | | |
| 92.5 PTH(1-34) | 680 ± 110 | 220 ± 30 | 3 | — | | 3 | N.B. | 4 |
| 521 PTH(1-14) | 140,000 ± 30,000 | 110 ± 10* | 3 | — | | 3 | N.B. | 3 |
| 621 [M]PTH(1-14) | 40 ± 2.0 | 220 ± 20 | 3 | — | | 3 | 17,400 ± 1,400 | 3 |
| 674 [Aib$^{1,3}$M]PTH(1-21) | 0.38 ± 0.10 | 240 ± 20 | 3 | N.D. | | | 27 ± 1 | 6 |
| 671 [Aib$^{1,3}$M]PTH(1-14) | 0.73 ± 0.16 | 250 ± 20 | 3 | 130 ± 30 | 3.1 ± 0.2 | 3 | 1,600 ± 200 | 4 |
| 682 [Aib$^{1,3}$M]PTH(1-11) | 2.00 ± 0.40 | 220 ± 20 | 3 | N.D. | | | 13,000 ± 1,000 | 3 |
| 684 [Aib$^{1,3}$M]PTH(1-10) | 53,000 ± 10,000 | 84 ± 4* | 3 | N.D. | | | N.B. | 3 |

The peptides were derivatives of rat PTH with C-terminal carboxamides; in PTH(1-14) and shorter analogs, "M" refers to the amino acid modifications: Ala$^{3,12}$, Gln$^{10}$, Har$^{11}$, Trp$^{14}$, unless the residue position was absent due to truncation or replaced by Aib (α-aminoisobutyric acid); in the PTH(1-21) analog, "M" refers to the same modifications and the modificationsof Nle$^8$, Arg$^{19}$ and Tyr$^{21}$.
Peptides were evaluated in COS-7 cells transiently transected with either the wild-type hP1R (hP1R-WT), or a truncated hP1R lacking most of the amino-terminal extracellular domain (hP1R-delNt).
The basal levels of cAMP were 10.3 ± 1.1 and 9.5 ± 1.3 picomole per well for hP1R-WT and hP1R-delNt, respectively.
The basal levels of $^3$H-inositol phosphates were 1,103 ± 143 and 2,929 ± 877 cpm per well for hP1R-WT and hP1R-delNt, respectively.
The Emax$^{(obs.)}$ (maximum response observed) values in the cAMP and PLC assays were determined at ligand doses of 0.1 to 100 µM; an asterisk indicated that a plateau in the response curve was not attained and the curve-fitting equation used to determine the EC$_{50}$ was constrained to within one standard deviation of the maximum response observed with the same receptor in the same assay.
Competition binding assays were performedwith $^{125}$I-[Aib$^{1,3}$, M]PTH(1-21) radioligand as tracer.
Values are means (± S.E.M.) of data from the number of independent experiments indicated (n), each of which was performed in duplicate.
A dashed line indicates that no cAMP or PLC response was observed.
N.B. indicates that no inhibition of tracer binding was observed.
N.D. indicates that the experiment was not done.

Example 3

Activity in Bone Cells

Figure 4:
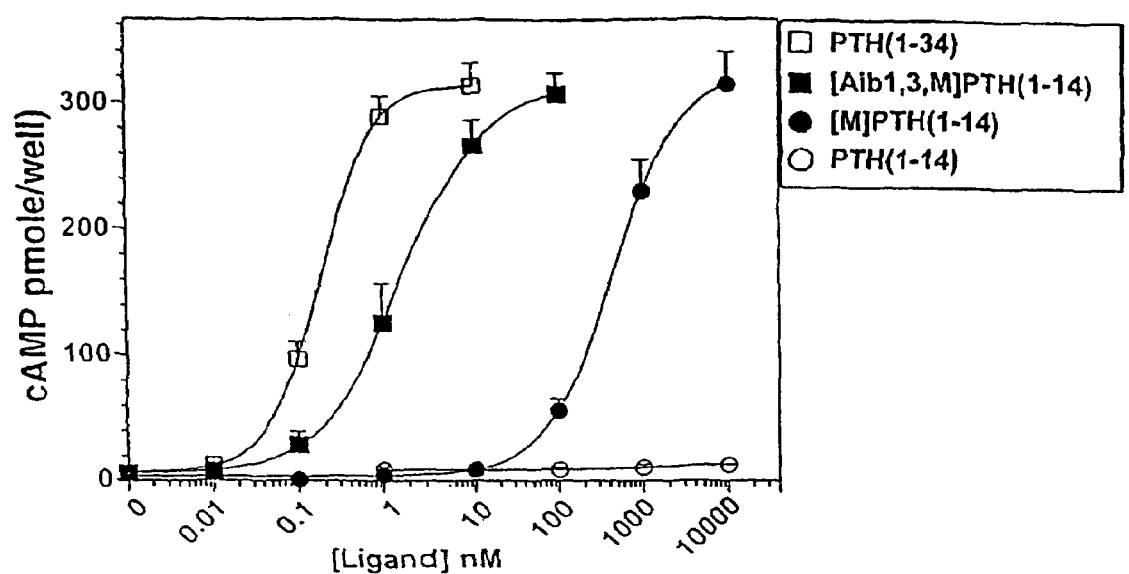
FIG. 4. cAMP-signaling properties of PTH analogs in SaOS-2 cells. The peptides, PTH(1-34), native PTH(1-14), [M]PTH(1-14) and [Aib$^{1,3}$,M]PTH(1-14) were evaluated in the human osteosarcoma-derived cell line SaOS-2 for the capacity to stimulate intracellular cAMP accumulation. Shown are combined data (mean±S.E.M.) from 3 or 4 experiments, each performed in duplicate. Symbols are defined in the Key.

The number of PTH-1 receptors expressed on the surface of the PTH target cells in bone or kidney is uncertain, but it is likely to be considerably lower than that found in HKRK-B28 cells. Therefore, several of the Aib-mounted PTH analogs were evaluated using SaOS-2 cells. These cells were derived from a human osteosarcoma, exhibited osteoblast-like properties and endogenously expressed relatively low levels of the PTH-1 receptor (~20,000 receptors/cell (Marx, U. C., et al., *J. Biol. Chem.* 273:4308-4316 (1998)). In these cells, [Aib$^1$,M] PTH(1-14) and [Aib$^3$,M]PTH(1-14) were 15- and 8-fold more potent in stimulating cAMP formation than was [M]PTH(1-14), and [Aib$^{1,3}$,M]PTH(1-14) was 130-fold more potent than [M]PTH(1-14) (FIG. 4 and Table 3). Thus, in SaOS-2 cells, [Aib$^{1,3}$,M]PTH(1-14) was only 13-fold less potent than PTH(1-34) and at least five-orders of magnitude more potent than native PTH(1-14), for which no activity could be detected, even at a dose of 10 µM (FIG. 4).

Figure 5:
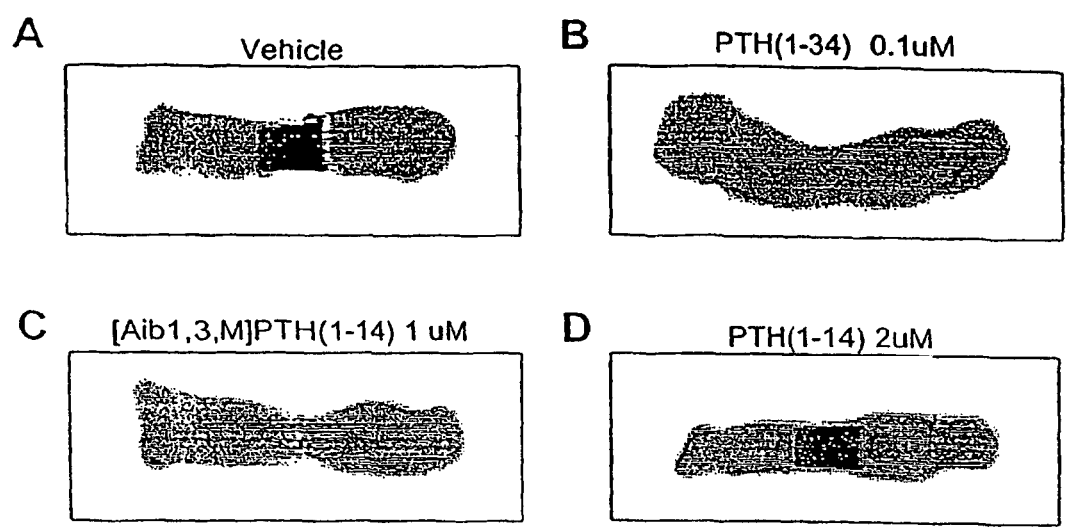
FIG. 5. Effect of PTH analogs on bone mineralization in embryonic mouse metatarsals. Cartilaginous metatarsal bone rudiments were excised from E15.5 mouse embryos and transferred to tissue culture plates containing serum-free media. Added to the samples for 48 h were vehicle: (A); PTH(1-34) (0.1 µM) (B); [Aib$^{1,3}$,M]PTH(1-14) (1 µM) (C) or native PTH(1-14) (2 µM) (D). Samples were explanted and incubated at 37° C. for a total of 64 h; peptide or vehicle were added at 16 h and again at 24 h. At the end of the incubation, the samples were fixed, sectioned and directly visualized under white light using a dissecting scope. In the vehicle- and native PTH(1-14)-treated samples mineralization can be detected as dark material at the center of the bone rudiment. Both PTH(1-34) and [Aib$^{1,3}$,M]PTH(1-14) inhibited mineralization. Shown are data from a single experiment, comparable results were obtained in three other replicate experiments.

Whether or not [Aib$^{1,3}$,M]PTH(1-14) activity could be detected in a more intact bone system was studied in an explant assay. An explant assay utilized cartilaginous metatarsal rudiments isolated from E15.5mouse embryos and subsequently cultured in multi-well plates containing serum-free media. A PTH peptide analog or vehicle control, was added to the culture 16 h after explantation, then again at 24 h. The incubation was terminated 24 h later for a total of 48 h of treatment over a 64 h period. In the absence of PTH, chondrocyte differentation occurred, such that by the end of the experiment, dense mineralization was apparent at the bone's mid-section (FIG. 5A). Differentiation was inhibited by the presence of PTH(1-34) (0.1 µM) or [Aib$^{1,3}$,M]PTH(1-14) (1µM), as no mineralization was observed (FIGS. 5, B and C). Mineralization was also inhibited in these assays by [Aib$^{1,3}$, M]PTH(1-14), whereas no effect could be detected for native PTH(1-14) (2 µM) (FIG. 5D). Comparable results were obtained in each of three replicate experiments. In addition, mRNA in situ hybridization analysis performed on the explanted metatarsals demonstrated that both PTH(1-34) and [Aib$^{1,3}$,M]PTH(1-14) inhibited expression of the collagen X gene, a bone developmental marker gene (data not shown). These inhibitory effects were consistent with the known capacity of PTHRP to retard chondrocyte differentiation in the growth plate cartilage of developing long bones (Pellegrini, M., et al., *Biochemistry* 37:12737-12743 (1998)).

TABLE 3 cAMP Stimulation in SaOS-2 cells

| | Peptide | EC$_{50}$ nM | EMAX$_{(obs.)}$ pmole/well | n |
|---|---|---|---|---|
| 93 | PTH (1-34) | 0.2 ± 0.02 | 350 ± 30 | 4 |
| 621 | [M]PTH(1-14) | 340 ± 120 | 340 ± 30 | 4 |
| 521 | PTH(1-14) | N.R. | | 2 |
| 622 | [Aib$^1$, M]PTH(1-14) | 22 ± 4 | 340 ± 30 | 4 |
| 624 | [Aib$^3$, M]PTH(1-14) | 42 ± 8 | 330 ± 30 | 4 |
| 671 | [Aib$^{1,3}$, M]PTH(1-14) | 2.6 ± 0.5 | 320 ± 30 | 3 |

The peptides PTH(1-34) ([Nle$^{8,21}$, Tyr$^{34}$]PTH(1-34)amide), [M]PTH(1-14) (m = Ala$^{3,12}$, Gln$^{10}$, Har$^{11}$, Trp$^{14}$), native PTH(1-14), and analogs of[M]PTH (1-14) containing α-aminoisobutyric acid (Aib) at positions 1 and/or 3, were evaluated for the capacity to stimulate cAMP production in the human osteoblastic cell line SaOS-2.
The calculated EC50 values and observed maximum response values are means (± S.E.M.) of data from the number of experiments indicated (n).
The basal cAMP level was 6.4 ± 0.8 (n = 4).
N.R. indicates that no cAMP response was detected.

Example 4

Circular Dichroism

Figure 6:
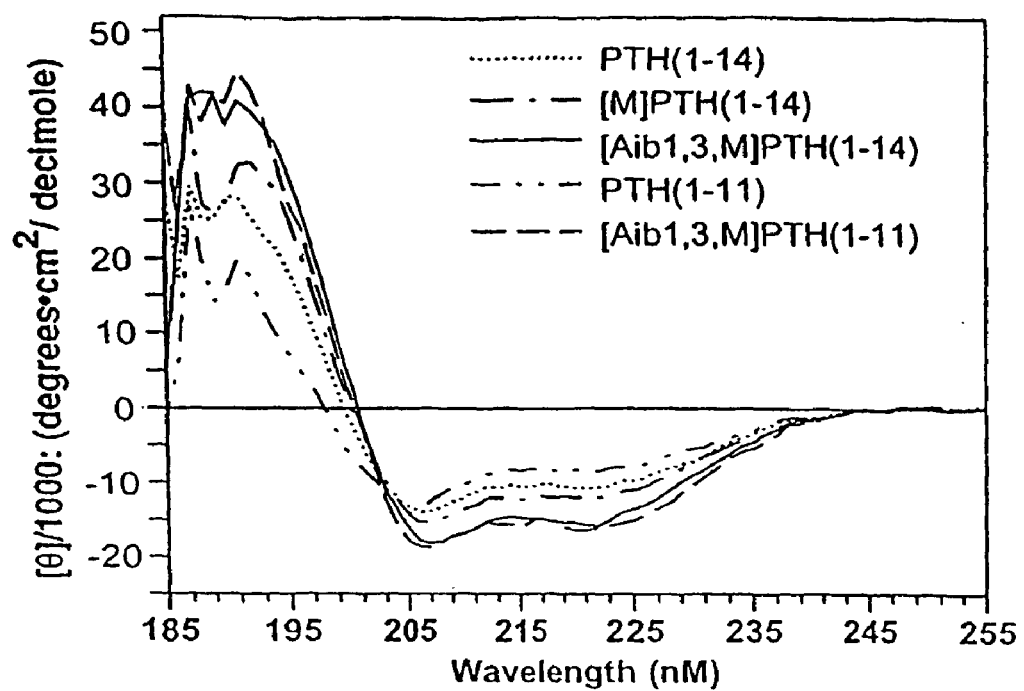
FIG. 6. Circular Dichroism Spectroscopy. Spectra were recorded for the indicated N-terminal PTH oligopeptides, each at 20 µM, in 50 nM sodium phosphate buffer, pH 7.4 containing 20% 2,2,2,-trifluoroethanol. The negative extrema in the spectra at ~209 nM and ~222 nM, and the positive extrema at ~192 nM, which are more apparent in the Aib-containing PTH analogs, as compared to the non-Aib-containing peptides, are indicative of helical content.

Circular dichroism (CD) spectroscopy was used to analyze the potential effects that the Aib substitutions had on peptide secondary structure when the peptides were free in solution. Samples were analyzed in both aqueous phosphate buffer and in phosphate buffer containing 2,2,2-trifloroethanol, an organic solvent which promotes helical structure in oligopeptides, including PTH peptide fragments (Pellegrini, M., et al., *J. Biol. Chem.* 273:10420-10427 (1998); Gronwald, W., et al., *Biol. Chem. Hoppe Seyler* 377:175-186 (1996); Barden, J.A., and Kemp, B. E., *Biochemistry* 32:7126-7132 (1993)). In phosphate buffer, the helical content of each peptide, estimated from the elipticity observed at 222 nM, was small (≦16%); however, [Aib$^{1,3}$,M]PTH(1-14) contained nearly twice as much helix as did [M]PTH(1-14) (16% and 8.1% respectively), as did [Aib$^{1,3}$,M]PTH(1-1l), as compared to [M]PTH(1-1) (13% and 7.5% respectively, Table 4). In 2,2, 2-trifluoroethanol, the helical content of each peptide increased; [Aib$^{1,3}$,M]PTH(1-14) and [Aib$^{1,3}$,M]PTH(1-11) exhibited the two highest levels of helical content (56% and 57%, respectively) and were each more helical than their Ala-1,-3-containing counterpart peptides (FIG. 6 and Table 4). The higher helical contents of these two peptides were evident not only from the negative elipticities at 192 nM and 222 nM, but also from the positive elipticities at 192 nM (FIG. 6). Unmodified PTH(1-11) exhibited the least amount of helical structure (30%), whereas [Aib$^{1,3}$,M]PTH(1-10) was approximately 47% helical (FIG. 6 and Table 4). These results suggest that the Aib-1,3 modifications increase the helical structure of the N-terminal PTH oligo peptides in the free solution phase.

TABLE 4

Helicity in N-terminal PTH peptides

| | [0]$_{222}$obs × 10$^{-3}$ | | helical residues (%) | |
|---|---|---|---|---|
| peptide | Phos. | Phos + TFE | Phos. | Phos + TFE |
| PTH(1-14) | −2.6 | −10.6 | 9.1 | 38 |
| [M]PTH(1-14) | −2.3 | −11.9 | 8.1 | 42 |
| Aib$^{1,3}$, M]PTH(1-14) | −4.6 | −15.7 | 16 | 56 |
| PTH(1-11) | −1.8 | −8.4 | 6.5 | 30 |
| [M]PTH(-11) | −2.1 | −9.9 | 7.5 | 35 |
| [Aib$^{1,3}$, M]PTH(1-11) | −3.7 | −16.1 | 13 | 57 |
| [Aib$^{1,3}$, M]PTH(1-10) | −3.2 | −13.1 | 11 | 47 |

Circular dichroism spectra were recorded in either 50 mM phosphate buffer or 50 mM phosphate buffer containing trifluoroethanol (20%) as described in Material and Methods and shown in FIG. 6.
The mean residue elipticity ([0]$_{222}^{obs}$/[0]$_{222}^{max}$) × 100; where [0]$_{222}$ obs is the mean residue elipticity at 222 nM observed for that peptide and [0]$_{222}$ max is the mean residue elipticityreported for a model helical peptide of 10 amino acids (−28.1 × 10$^{-3}$; Yang et al. 1986 Methods in Enzymol. 130, 208-269).

Example 5

PTH Analogs

As the first step, Aib was introduced at each position in [M]PTH(1-14). The Aib-scanning data indicated that substitutions at most positions diminished activity. However, the Aib scan data revealed considerable (8- to 10-fold) improvements in cAMP signaling potency with substitutions at position one and three, and these effects were additive, as [Aib$^{1,3}$,M]PTH(1-14), with an EC$_{50}$ of ~1 nM in HKRK-B28 cells, was 100-fold more potent than [M]PTH(1-14), and at least as potent as PTH(1-34).

Competition binding studies performed with [125]I-[M]PTH (1-21) indicated that most of the Aib substitutions exerted their effects on potency (positive or negative), at least in part, by changing PTH-1 receptor-binding affinity. Thus, the Aib-1 and Aib-3 substitutions each improved the apparent affinity of [M]PTH(1-14) for HKRK-B28 cells by approximately 10-fold, and the combined Aib-1,3 substitution increased affinity by approximately 100-fold. Likewise, the decreases in cAMP signaling potency caused by most of the other Aib substitutions could be explained by decreases in apparent binding affinity, even though, overall, binding affinities were generally 10- to 100-fold weaker than the corresponding cAMP signaling potencies. Two exceptions to this were the peptides substituted at positions 2 and 6, at which signaling potency was comparable with (position 2) or ~10-fold weaker than the corresponding apparent binding affinity. That the substitution of Aib for valine-2 or glutamine-6 impaired signaling activity more than receptor-binding affinity, is consistent with the disproportionate reductions in signaling potency, relative to binding affinity, that occur with substitutions at these positions in PTH(1-34) analogs, and, in fact, result in PTH-1R antagonists (Cohen, F. E., et al., *J. Biol. Chem.* 266:1997-2004 (1991); Gardella, T. J., et al., *J. Biol. Chem.* 266:13141-13146(1991), Carter 1999 #1180).

The 100-fold increase in cAMP-stimulating potency effect that occurred with the paired Aib-1,3 modification to [M]PTH (1-14) seems consistent with the hypothesis that an α-helix in the N-terminal portion of PTH is required for activation of the PTH-1 receptor. The capacity of Aib to stabilize α-helical structure in oligopeptides arises from the steric restrictions on the rotations about the N-C° (φ) and C°-CO (ψ) bonds of the Aib residue that are imposed by the two methyl groups symmetrically bonded to its C° atom (Kaul, R., and Balaram, P., *Bioorganic & Medicinal Chemistry* 7:105-117 (1999); Burgess, A. W., and Leach, S. J., *Biopolymers* 12:2599-2605 (1973)). The φ and ψ torsion angles about this C° atom are tightly restricted to those that occur in α-helices but the symmetry of the di-allyl-substituted C° atom of Aib allows for either right-handed or left-handed α-helices. If the latter "reversed" configuration occurs in an otherwise right-handed helix, then the Aib residue will, in all probability, induce a turn, and thus terminate the helix (Kaul, R., and Balaram, P., *Bioorganic & Medicinal Chemistry* 7:105-117 (1999); Venkataram Prasad, B. V., et al., *Biopolymers* 18:1635-1646 (1979)). This reversed configuration is rare in peptide structures, relative to the right-handed configuration (Kaul, R., and Balaram, P., *Bioorganic & Medicinal Chemistry* 7:105-117 (1999)), but it nevertheless leaves open the possibility that Aib at the amino-terminus of PTH(1-14) enhances potency through some mechanism other than stabilization of an α-helix.

It is also of interest that the most beneficial effects on peptide potency/affinity occurred with Aib substitutions at positions 1 and 3, since none of the structural studies on PTH(1-34) analogs have detected structure N-terminal of residue 3. It may be that Aib at position 1 nucleates helix formation of "down-stream" residues within itself participating in the helix. Alternatively, the modification may induce or stabilize helical structure at the very N-terminus of the peptide which is simply too unstable in the native sequence to be detected by NMR spectroscopy or x-ray crystallography. In any case, the 1000-fold higher cAMP signaling potency exhibited by [Aib$^{1,3}$,Gln$^{10}$,Har$^{11}$]PTH(1-11) as compared to [Ala$^3$,Gln$^{10}$,Har$^{11}$]PTH(1-11) (EC$_{50}$s~6 nM Vs. 3 µM, respectively, Table 1 and (Shimizu, M., et al., *Endocrinology* (2001) (In Press)) demonstrates that the effects of the Aib substitutions are exerted locally, e.g. within the first 11 amino acids of the peptide.

Direct structural analyses of these analogs, as free peptides, or potentially in complex with the PTH-1 receptor, could provide valuable insights into the ligand structures that allow a ligand to act as an agonist on the PTH-1 receptor. In this regard, the information derived from the data set described herein could be of use in the design of peptide mimetics for the PTH-1 receptor. Approaching this problem from the standpoint of the native PTH peptide sequence is made difficult by the conformational diversity that is possible at each position in the peptide backbone chain. The incorporation of stereochemically constrained amino acids, such as Aib, into the peptide chain, lessens this problem, as it serves to nucleate predictable peptide structures. Thus, the approach can facilitate the de novo design of peptide or nonpeptide agonists for the PTH-1 receptor. Given the recently proven utility of PTH(1-34) in treating osteoporosis (Neer, R. M., et al., *N.E.J.M.* 344:1434-1441 (2001)), such agonists should have important medical impact.

At the molecular level, it is presently unclear how the [Aib$^{1,3}$,M]PTH analogs interact with the receptor; nor is this known for any PTH ligand, although fairly specific computer models of the interaction with native PTH are now being developed (Jin, L., et al., *J. Biol. Chem.* 275:27238-27244 (2000); Rölz, C., and Mierke, D. F., Biophysical Chemistry (2000) (In Press)). The above described experiments with the truncated PTH-1 receptor, P1R-delNt, provide some insights, as they demonstrate that the enhancing effects of the Aib substitutions at positions 1 and 3 are mediated through the juxtamembrane region (J domain) of the receptor containing the extracellular loops and transmembrane domains. This finding is consistent with the cumulative crosslinking and mutational data on the PTH/PTH-1 receptor interaction, which indicate that residues in the (1-14) domain of PTH interact primarily, if not exclusively, with the receptor's J domain, as opposed to its amino-terminal extracellular domain (N domain) (Bergwitz, C., et al., *J. Biol. Chem.* 271: 26469-26472 (1996); Hoare, S. R. J., et al., *J. Biol. Chem* 276:7741-7753 (2001); Behar, V., et al., *J. Biol. Chem.* 275: 9-17 (1999); Shimizu, M., et al., *J. Biol. Chem.* 275:19456-19460 (2000); Luck, M. D., et al., *Molecular Endocrinology* 13:670-680 (1999); Shimizu, M., et al., *J. Biol. Chem.* 275: 21836-21843 (2000); Carter, P. H., and Gardella, T. J., *Biochim. Biophys. Acta* 1538:290-304 (2001); Gardella, T. J., et al., *Endocrinology* 132:2024-2030 (1993); Bisello, A., et al., *J. Biol. Chem.* 273:22498-22505 (1998)).

Another important conclusion to derive from our study with P1R-delNt, in which [Aib$^{1,3}$,M]PTH(1-14) exhibited low nanomolar potency and full efficacy in cAMP assays and nearly fill efficacy in PLC assays, is that the truncated receptor, which lacks nearly all of the N domain, is capable of mounting a sensitive and robust response to a small agonist ligand. The availability of a radioligand that binds to the P1R-delNt, $^{125}$I-[Aib$^{1,3}$,M]PTH(1-21), enabled, for the first time, binding studies to be performed on this truncated receptor. Scatchard analysis of our homologous competition binding data yielded Bmax values for P1R-delNt that were not significantly different from those observed for P1R-WT (1.3±0.1 receptors/cell Vs. 1.9±0.8 receptors/cell, respectively, P=0.3). Thus, the truncated receptor is well expressed on the surface of COS-7 cells. Not surprisingly, PTH(1-34) failed to inhibit the binding of $^{125}$I-[Aib$^{1,3}$,M]PTH(1-21) to P1R-delNt, a result which highlights the importance of the interaction between the N domain of the receptor and the C-terminal (15-34) domain of the native peptide in stabilizing the overall hormone-receptor complex. This result also supports the view that the interaction between the amino-terminal portion of PTH and the J domain of the receptor is of very weak affinity (Hoare, S. R. J., et al., *J. Biol. Chem* 276:7741-7753 (2001)). Clearly, the affinity of the interaction can be improved considerably, as the apparent affinity with which [Aib$^{1,3}$,M]PTH(1-14) bound to P1R-delNt (IC$_{50}$ ~1,500 nM) was much greater than that of native PTH(1-14), which failed to inhibit tracer binding. The 50-fold difference that we observed in the affinities with which [Aib$^{1,3}$,M]PTH(1-14) and [Aib$^{1,3}$,M]PTH(1-21) bound to P1R-delNt shows that residues C-terminal of residue 14 (e.g., residues 15-21) contribute binding interactions to the J domain of the receptor. Studies on related analogs suggest that at least some of this effect involves residue 19.

In summary, highly potent PTH(1-14) analogs are obtained by introducing the conformationally constrained amino acid, Aib, at the N-terminus of the peptide. The propensity of Aib to stabilize α-helical structure, and the high potency with which the modified analogs activated P1R-delNt, show that the N-terminal portion of PTH is α-helical when it is bound to the activation domain of the receptor. The results also establish that the activation domain of the PTH-1R, as defined by P1R-delNt, is fully capable of mediating high affinity and productive interactions with an agonist ligand.

Example 6

PTH(1-34) Derivatives

We have found that Aib substitutions at positions 1 and 3 in PTH(1-34) ([Tyr34]hPTH(1-34)amide) improve cAMP-stimulating potency on P1R-delNT expressed in COS-7 cells by ~100-fold, relative to unmodified PTH(1-34) (see Table 5 and FIG. 7B). The Aib substitutions do not detectably improve potency of PTH(1-34) on the intact wild-type PTH-1 receptor in COS-7 cells (Table 5, and FIG. 7A); a result which may be due to the already maximal response mediated by native PTH(1-34) in these cells which express very high levels of the intact receptor. In a less sensitive cell system, such as with the delNT receptor, in which nearly the entire amino-terminal extracellular domain of the receptor is deleted, or perhaps in bone cells in animals expressing low levels of endogenous PTH receptors, the effect of Aib-1,3 substitutions on PTH(1-34) potency are significant. Peptides with other, above described modifications (e.g. Gln10, homoArg11, Ala12, Trp14, Arg19) are much more potent than PTH(1-34) in COS-7 cells expressing hP1R-delNT as well. For example, [Aib$^{1,3}$,Gln$^{10}$,Har$^{11}$, Ala$^{12}$,Trp$^{14}$,Arg$^{19}$, Tyr$^{34}$]hPTH(1-34) has an EC50 value of 1.9±0.6 nM on P1R-delNT. It is expected that the above described modifications will also be much more potent than PTH(1-34) in other native bone cell systems of low sensitivity.

TABLE 5 cAMP Responses of hPTH(1-34) Analogs in COS-7 Cells

| peptide | EC50(nM) hP1R-WT | EC50(nM) hP1R-delNt |
|---|---|---|
| [Tyr$^{34}$]-hPTH(1-34) | 0.44 ± 0.02 | 2,800 ± 300 |
| [Aib$^{1,3}$, Tyr$^{34}$]-hPTH(1-34) | 0.67 ± 0.18 | 43 ± 24 |

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned hereinabove are herein incorporated in their entirety and by reference to the same extent as if each individual publication, patent or patent application was specifically and individually indicated to be incorporated by reference.

What is claimed is:

1. A biologically active peptide comprising a formula selected from:
   (a) $X_{01}ValX_{02}GluIleGlnLeuMetHisX_{03}X_{04}X_{05}X_{05}X_{06}X_{07}$ (SEQ ID NO. 1);
   (b) fragments thereof, containing amino acids 1-10, 1-11, 1-12 or 1-13; or
   (c) pharmaceutically acceptable salts thereof; wherein:
   $X_{01}$ is Aib, desaminoGly, desaminoSer or desaminoAla;
   $X_{02}$ is Aib, Ala, or Ser;
   $X_{03}$ is Ala, Gln or Asn;
   $X_{04}$ is Arg, Har or Leu;
   $X_{05}$ is Aib, Ala or Gly;
   $X_{06}$ is Aib or Lys;
   $X_{07}$ is Aib, Trp or His; and
   wherein at least one of $X_{01}$, $X_{02}$, $X_{05}$, $X_{06}$ or $X_{07}$ is Aib; and wherein said peptide is 20 amino acids or fewer in length.

2. The peptide of claim 1, wherein said peptide is selected from:
   (a) AibValSerGluIleGlnLeuMetHisAsnLeuGlyLysHis (SEQ ID NO. 2);
   (b) fragments thereof, containing amino acids 1-10, 1-11, 1-12 or 1-13; or
   (c) pharmaceutically acceptable salts thereof.

3. The peptide of claim 1, wherein said peptide is selected from:
   (a) desaminoAlaValAibGluIleGln-LeuMetHisAsnLeuGlyLysHis (SEQ ID NO. 3);
   (b) fragments thereof, containing amino acids 1-10, 1-11, 1-12 or 1-13; or
   (c) pharmaceutically acceptable salts thereof.

4. The peptide of claim 1, wherein said peptide is selected from:
  (a) desaminoSerValAibGluIleGlnLeuMetHisAsnLeuGlyLysHis (SEQ ID NO. 4);
  (b) fragments thereof, containing amino acids 1-10, 1-11, 1-12 or 1-13; or
  (c) pharmaceutically acceptable salts thereof.

5. The peptide of claim 1, wherein said peptide is selected from:
  (a) desaminoGlyValAibGluIleGlnLeuMetHisAsnLeuGlyLysHis (SEQ ID NO. 5);
  (b) fragments thereof, containing amino acids 1-10, 1-11, 1-12 or 1-13; or
  (c) pharmaceutically acceptable salts thereof.

6. The peptide of claim 1, wherein said peptide is selected from:
  (a) AibValAibGluIleGlnLeuMetHisGlnHarGlyLysTrp (SEQ ID NO. 6);
  (b) fragments thereof, containing amino acids 1-10, 1-11, 1-12 or 1-13; or
  (c) pharmaceutically acceptable salts thereof.

7. The peptide of claim 1, said peptide selected from:
  (a) AibValAibGluIleGlnLeuMetHisAsnLeuGlyLysHis (SEQ ID NO. 7);
  (b) fragments thereof, containing amino acids 1-10, 1-11, 1-12 or 1-13; or
  (c) pharmaceutically acceptable salts thereof.

8. The peptide of claim 1, said peptide selected from:
  (a) AibValAlaGluIleGlnLeuMetHisGlnHarAlaLysTrp (SEQ ID NO. 9);
  (b) fragments thereof, containing amino acids 1-10, 1-11, 1-12 or 1-13; or
  (c) pharmaceutically acceptable salts thereof.

9. The peptide of claim 1, wherein said peptide is AibValSerGluIleGlnLeuMetHisAsnLeuGlyLysHis (SEQ ID NO. 2).

10. The peptide of claim 1, wherein said peptide is desaminoAlaValAibGluIleGlnLeuMetHisAsnLeuGlyLysHis (SEQ ID NO. 3).

11. The peptide of claim 1, wherein said peptide is desamino SerValAibGluIleGlnLeuMetHisAsnLeuGlyLysHis (SEQ ID NO. 4).

12. The peptide of claim 1, wherein said peptide is desaminoGlyValAibGluIleGlnLeuMetHisAsnLeuGlyLysHis (SEQ ID NO. 5).

13. The peptide of claim 1, wherein said peptide is AibValAibGluIle GlnLeuMetHisGlnHarGlyLysTrp (SEQ ID NO. 6).

14. The peptide of claim 1, wherein said peptide is AibValAibGluIle GlnLeuMetHisAsnLeuGlyLysHis (SEQ ID NO. 7).

15. The peptide of claim 1, wherein said peptide is AibValAlaGluIle GlnLeuMetHisGlnHarAlaLysTrp (SEQ ID NO. 9).

16. The peptide of claim 1 or 12, wherein said peptide is labeled.

17. The peptide of claim 16, wherein said peptide is labeled with a fluorescent label.

18. The peptide of claim 16, wherein said peptide is labeled with a chemiluminescent label.

19. The peptide of claim 16, wherein said peptide is labeled with a bioluminescent label.

20. The peptide of claim 16, wherein said peptide is labeled with a radioactive label.

21. The peptide of claim 20, wherein said peptide is labeled with $^{125}$I.

22. The peptide of claim 20, wherein said peptide is labeled with $^{99m}$Tc.

23. A pharmaceutical composition comprising the biologically active peptide of claim 1, and a pharmaceutically acceptable carrier.

24. A method for treating mammalian conditions characterized by decreases in bone mass, said method comprising administering to a subject in need thereof an effective bone mass-increasing amount of a composition comprising a biologically active peptide of claim 1 and a pharmaceutically acceptable carrier.

25. The method of claim 24, wherein said condition to be treated is osteoporosis.

26. The method of claim 24, wherein said condition to be treated is old age osteoporosis.

27. The method of claim 24, wherein said condition to be treated is post-menopausal osteoporosis.

28. The method of claim 24, wherein said effective amount of said peptide for increasing bone mass is from about 0.01 µg/kg/day to about 1.0 µg/kg/day.

29. The method of claim 24, wherein the method of administration is parenteral.

30. The method of claim 24, wherein the method of administration is subcutaneous.

31. The method of claim 24, wherein the method of administration is nasal insufflation.

32. A method of making the peptide of claim 1, said method comprising the steps of:
  (a) attaching the C-terminal amino acid of SEQ ID NO:1 to a solid phase resin; and
  (b) extending the peptide in the N-terminal direction by successively coupling a protected form of the next amino acid, thereby synthesizing said peptide.

33. The method of making the peptide of claim 32, wherein said amino acid of step (b) is protected by FMOC.

34. The peptide of claim 1 consisting essentially of the peptide of SEQ ID NO:1.

35. The peptide of claim 1, wherein said peptide is a fragment of SEQ ID NO:1 containing amino acids 1-11.

36. The peptide of claim 1, wherein $X_{01}$ or $X_{02}$ is Aib.

37. The peptide of claim 36, wherein $X_{01}$ is Aib.

38. The peptide of claim 36, wherein $X_{02}$ is Aib.

39. The peptide of claim 36, where $X_{01}$ and $X_{02}$ are Aib.

40. The peptide of claim 1, wherein said peptide is 14 amino acids in length.

* * * * *

UNITED STATES PATENT AND TRADEMARK OFFICE
CERTIFICATE OF CORRECTION

| | |
|---|---|
| PATENT NO. | : 7,572,765 B2 |
| APPLICATION NO. | : 10/484080 |
| DATED | : August 11, 2009 |
| INVENTOR(S) | : Gardella et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C 154(b) by 1019 days.

Signed and Sealed this
Eighteenth Day of January, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,572,765 B2 | Page 1 of 3 |
| APPLICATION NO. | : 10/484080 | |
| DATED | : August 11, 2009 | |
| INVENTOR(S) | : Gardella | |

It is certified that error appears in the above-identified patent and that said Letters Patent is hereby corrected as shown below:

Cover Page, under INVENTOR, replace "Thomas J. Gardella, Boston, MA (US)" with --Thomas J. Gardella, Needham, MA (US), Naoto Shimizu, Shizuoka, Japan (JP), Henry M. Kronenberg, Belmont, MA (US), John T. Potts, Jr., Newton, MA (US)--.

Column 1, Line 66, replace "t6" with --to--.

Column 3, Line 24, replace "ofthe" with --of the--;

Line 34, replace "amnide" with --amide--;

Lines 36-38, replace "AibValAibGluIleGlnLeuNleHisGlnHarAlaLysTrpLeu-AlaSerValArgArtTyr (SEQ ID NO. 8)" with --AibValAibGluIleGlnLeuNleHisGlnHarAlaLysTrpLeuAlaSerValArgArgTyr (SEQ ID NO. 8)--;

Lines 57-59, replace "SerValAibGluIleGffiuMetHisGlnHarAlaLysTrp (SEQ ID NO. 11)" with --SerValAibGluIleGlnLeuMetHisGlnHarAlaLysTrp (SEQ ID NO. 11)--.

Column 4, Line 42, replace "ofthe" with --of the--;

Line 53, replace "$X_7$" with --$X_{07}$--;

Lines 64-65 replace "1-aminocyclopropylcarboxylic acid" with --1 aminocyclopentanecarboxylic acid--.

Column 6, Line 18, replace "synthesis. in another" with --synthesis. In another--;

Signed and Sealed this
Tenth Day of January, 2012

David J. Kappos
*Director of the United States Patent and Trademark Office*

CERTIFICATE OF CORRECTION (continued)
U.S. Pat. No. 7,572,765 B2

Column 6, Line 56, replace "iine" with --line--.

Column 9, Line 61, replace "($\leqq$PTH1-14)" with --($\leq$PTH1-14)--.

Column 10, Line 59, replace "ofthe" with --of the--.

Column 11, replace " "ofthe" with --of the--.

Column 12, Line 55, replace "usefull" with --useful--.

Column 14, Line 22, replace "PTI/PTHrP" with --PTH/PTHrP--.

Column 16, Line 12, replace "αXMEM" with --αMEM--;

Line 28, replace "preformed" with --performed--;

Line 63, replace "maximun" with --maximum--.

Column 17, Line 8, replace "($\leqq$PTH0.01) with --($\leq$PTH0.01)--;

Line 12, replace "10-14. were" with --10-14 were--;

Line 39, replace "[M] PTH(1-2)" with --[M] PTH(1-21)--.

Column 21, Line 50, replace "$_3$,M" with --$^3$,M--;

Line 52, replace "tranfected" with --transfected--.

Columns 21 and 22, under TABLE 2, replace "modificationsof" with --modifications of--;

Under TABLE 2, Replace "performedwith" with --performed with--.

Column 23, Line 66, replace "(C$\leqq$16%)" with --(C$\leq$16%)--.

Column 24, Line 2, replace "[M] PTH(1-1)" with --[M] PTH(1-11)--;

Under TABLE 4, Line 35, replace "elipticityreported" with --elipticity reported--.

Column 25, Line 22, replace "di-allyl" with --di-alkyl--.

Column 53, Line 55, replace "$X_{01}ValX_{02}GluIleLeuMetHisX_{03}X_{04}X_{05}X_{05}X_{06}X_{07}$"

CERTIFICATE OF CORRECTION (continued)
U.S. Pat. No. 7,572,765 B2 with --$X_{01}ValX_{02}GluIleLeuMetHisX_{03}X_{04}X_{05}X_{06}X_{07}$--.

Column 55, Line 17, replace "AibValAibGluIleGlnLeuMetHisGlnHarGlyLysTrp (SEQ ID NO. 6)" with --AibValAibGluIleGlnLeuMetHisGlnHarAlaLysTrp (SEQ ID NO. 6)--;

Lines 46-48, replace "AibValAibGluIleGlnLeuMetHisGlnHarGlyLysTrp (SEQ ID NO. 6)" with --AibValAibGluIleGlnLeuMetHisGlnHarAlaLysTrp (SEQ ID NO. 6)--;

Line 55, replace "The peptide of claim 1 or 12" with --The peptide of claim 1--.

Disclaimer

7,572,765 B2 — Thomas J. Gardella, Needham, MA (US). CONFORMATIONALLY CONSTRAINED PARATHYROID HORMONE (PTH) ANALOGS. Patented date August 11, 2009. Disclaimer filed December 27, 2012 by the Patentee.

Hereby enter this disclaimer for claim 13.

*(Official Gazette, March 26, 2013)*

UNITED STATES PATENT AND TRADEMARK OFFICE
CERTIFICATE OF CORRECTION

| | | |
|---|---|---|
| PATENT NO. | : 7,572,765 B2 | Page 1 of 1 |
| APPLICATION NO. | : 10/484080 | |
| DATED | : August 11, 2009 | |
| INVENTOR(S) | : Thomas J. Gardella | |

It is certified that error appears in the above-identified patent and that said Letters Patent is hereby corrected as shown below:

In the Specification

Column 1, Line 4, insert:
-- STATEMENT AS TO FEDERALLY FUNDED RESEARCH
This invention was made with government support under DK011794 awarded by the National Institutes of Health. The government has certain rights in the invention. --

Signed and Sealed this
Second Day of May, 2023

*Katherine Kelly Vidal*

Katherine Kelly Vidal
*Director of the United States Patent and Trademark Office*

```
                        SEQUENCE LISTING

<160> NUMBER OF SEQ ID NOS: 31

<210> SEQ ID NO 1
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: VARIANT, MOD_RES
<222> LOCATION: (1)..(1)
<223> OTHER INFORMATION: alpha-helix stabilizing residue, desamino Gly,
      desamino Ser or desamino Ala
<220> FEATURE:
<221> NAME/KEY: VARIANT, MOD_RES
<222> LOCATION: (3)..(3)
<223> OTHER INFORMATION: alpha-helix stabilizing residue, Ala or Ser
<220> FEATURE:
<221> NAME/KEY: VARIANT
<222> LOCATION: (10)..(10)
<223> OTHER INFORMATION: Gln, Asn or Ala
<220> FEATURE:
<221> NAME/KEY: VARIANT, MOD_RES
<222> LOCATION: (11)..(11)
<223> OTHER INFORMATION: Homoarginine, Leu or Arg
<220> FEATURE:
<221> NAME/KEY: VARIANT, MOD_RES
<222> LOCATION: (12)..(12)
<223> OTHER INFORMATION: alpha-helix stabilizing residue, Gly or Ala
<220> FEATURE:
<221> NAME/KEY: VARIANT, MOD_RES
<222> LOCATION: (13)..(13)
<223> OTHER INFORMATION: alpha-helix stabilizing residue or Lys
<220> FEATURE:
<221> NAME/KEY: VARIANT,MOD_RES
<222> LOCATION: (14)..(14)
<223> OTHER INFORMATION: alpha-helix stabilizing residue, Trp or His

<400> SEQUENCE: 1
```

Xaa Val Xaa Glu Ile Gln Leu Met His Xaa Xaa Xaa Xaa Xaa
1               5                   10

<210> SEQ ID NO 2
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: Aib

<400> SEQUENCE: 2

Xaa Val Ser Glu Ile Gln Leu Met His Asn Leu Gly Lys His
1               5                   10

<210> SEQ ID NO 3
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: desamino Ala
<220> FEATURE:
<221> NAME/KEY: MOD_RES
<222> LOCATION: (3)..(3)
<223> OTHER INFORMATION: Aib

<400> SEQUENCE: 3

Xaa Val Xaa Glu Ile Gln Leu Met His Asn Leu Gly Lys His
1               5                   10

<210> SEQ ID NO 4
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: desamino Ser
<220> FEATURE:
<221> NAME/KEY: MOD_RES
<222> LOCATION: (3)..(3)
<223> OTHER INFORMATION: Aib

<400> SEQUENCE: 4

Xaa Val Xaa Glu Ile Gln Leu Met His Asn Leu Gly Lys His
1               5                   10

<210> SEQ ID NO 5
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: desamino Gly
<220> FEATURE:
<221> NAME/KEY: MOD_RES
<222> LOCATION: (3)..(3)
<223> OTHER INFORMATION: Aib

<400> SEQUENCE: 5

Xaa Val Xaa Glu Ile Gln Leu Met His Asn Leu Gly Lys His
1               5                   10

<210> SEQ ID NO 6
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Homoarginine

<400> SEQUENCE: 6

Xaa Val Xaa Glu Ile Gln Leu Met His Gln Xaa Ala Lys Trp
1               5                   10

<210> SEQ ID NO 7
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib

<400> SEQUENCE: 7

Xaa Val Xaa Glu Ile Gln Leu Met His Asn Leu Gly Lys His
1               5                   10

<210> SEQ ID NO 8
<211> LENGTH: 21
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Homoarginine

<400> SEQUENCE: 8

Xaa Val Xaa Glu Ile Gln Leu Xaa His Gln Xaa Ala Lys Trp Leu Ala
1               5                   10                  15

Ser Val Arg Arg Tyr
            20

<210> SEQ ID NO 9
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (11)..(11)
<223> OTHER INFORMATION: Homoarginine

<400> SEQUENCE: 9

Xaa Val Ala Glu Ile Gln Leu Met His Gln Xaa Ala Lys Trp
1               5                   10

<210> SEQ ID NO 10
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Homoarginine

<400> SEQUENCE: 10

Ala Val Xaa Glu Ile Gln Leu Met His Gln Xaa Ala Lys Trp
1               5                   10

<210> SEQ ID NO 11
<211> LENGTH: 14
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Homoarginine

<400> SEQUENCE: 11

Ser Val Xaa Glu Ile Gln Leu Met His Gln Xaa Ala Lys Trp
1               5                   10

<210> SEQ ID NO 12
<211> LENGTH: 13
<212> TYPE: PRT
<213> ORGANISM: Artificial
<220> FEATURE:
<223> OTHER INFORMATION: Derivative of PTH polypeptide
<220> FEATURE:
<221> NAME/KEY: VARIANT, MOD_RES
<222> LOCATION: (1)..(1)
<223> OTHER INFORMATION: alpha-helix stabilizing residue, desamino Gly,
      desamino Ser or desamino Ala

```
<220> FEATURE:
<221> NAME/KEY: VARIANT, MOD_RES
<222> LOCATION: (3)..(3)
<223> OTHER INFORMATION: alpha-helix stabilizing residue, Ala, or Ser
<220> FEATURE:
<221> NAME/KEY: VARIANT
<222> LOCATION: (10)..(10)
<223> OTHER INFORMATION: Gln, Asn or Ala
<220> FEATURE:
<221> NAME/KEY: VARIANT, MOD_RES
<222> LOCATION: (11)..(11)
<223> OTHER INFORMATION: Homoarginine, Leu or Arg
<220> FEATURE:
<221> NAME/KEY: VARIANT, MOD_RES
<222> LOCATION: (12)..(12)
<223> OTHER INFORMATION: alpha-helix stabilizing residue, Gly or Ala

<400> SEQUENCE: 12

Xaa Val Xaa Glu Ile Gln Leu Met His Xaa Xaa Xaa Xaa
1               5                   10

<210> SEQ ID NO 13
<211> LENGTH: 12
<212> TYPE: PRT
<213> ORGANISM: Artificial
<220> FEATURE:
<223> OTHER INFORMATION: Derivative of PTH polypeptide
<220> FEATURE:
<221> NAME/KEY: VARIANT, MOD_RES
<222> LOCATION: (1)..(1)
<223> OTHER INFORMATION: alpha-helix stabilizing residue, desamino Gly,
      desamino Ser or desamino Ala
<220> FEATURE:
<221> NAME/KEY: VARIANT, MOD_RES
<222> LOCATION: (3)..(3)
<223> OTHER INFORMATION: alpha-helix stabiliizing residue, Ala or Ser
<220> FEATURE:
<221> NAME/KEY: VARIANT
<222> LOCATION: (10)..(10)
<223> OTHER INFORMATION: Gln, Asn or Ala
<220> FEATURE:
<221> NAME/KEY: VARIANT, MOD_RES
<222> LOCATION: (11)..(11)
<223> OTHER INFORMATION: Homoarginine, Leu or Arg
<220> FEATURE:
<221> NAME/KEY: VARIANT, MOD_RES
<222> LOCATION: (12)..(12)
<223> OTHER INFORMATION: alpha-helix stabilizing residue, Gly or Ala

<400> SEQUENCE: 13

Xaa Val Xaa Glu Ile Gln Leu Met His Xaa Xaa Xaa
1               5                   10

<210> SEQ ID NO 14
<211> LENGTH: 11
<212> TYPE: PRT
<213> ORGANISM: Artificial
<220> FEATURE:
<223> OTHER INFORMATION: Derivative of PTH polypeptide
<220> FEATURE:
<221> NAME/KEY: VARIANT, MOD_RES
<222> LOCATION: (1)..(1)
<223> OTHER INFORMATION: alpha-helix stabilizing residue, desamino Gly,
      desamino Ser or desamino Ala
<220> FEATURE:
<221> NAME/KEY: VARIANT, MOD_RES
<222> LOCATION: (3)..(3)
<223> OTHER INFORMATION: alpha-helix stabilizing residue, Ala, or Ser
<220> FEATURE:
<221> NAME/KEY: VARIANT
<222> LOCATION: (10)..(10)
<223> OTHER INFORMATION: Gln, Asn or Ala
<220> FEATURE:
<221> NAME/KEY: VARIANT, MOD_RES
<222> LOCATION: (11)..(11)
```

-continued

<223> OTHER INFORMATION: Homoarginine, Leu or Arg

<400> SEQUENCE: 14

Xaa Val Xaa Glu Ile Gln Leu Met His Xaa Xaa
1               5                   10

<210> SEQ ID NO 15
<211> LENGTH: 10
<212> TYPE: PRT
<213> ORGANISM: Artificial
<220> FEATURE:
<223> OTHER INFORMATION: Derivative of PTH polypeptide
<220> FEATURE:
<221> NAME/KEY: VARIANT, MOD_RES
<222> LOCATION: (1)..(1)
<223> OTHER INFORMATION: alpha-helix stabilizing residue, desamino Gly,
      desamino Ser or desamino Ala
<220> FEATURE:
<221> NAME/KEY: VARIANT, MOD_RES
<222> LOCATION: (3)..(3)
<223> OTHER INFORMATION: alpha-helix stabilizing residue, Ala, or Ser
<220> FEATURE:
<221> NAME/KEY: VARIANT
<222> LOCATION: (10)..(10)
<223> OTHER INFORMATION: Gln, Asn or Ala

<400> SEQUENCE: 15

Xaa Val Xaa Glu Ile Gln Leu Met His Xaa
1               5                   10

<210> SEQ ID NO 16
<211> LENGTH: 11
<212> TYPE: PRT
<213> ORGANISM: Artificial
<220> FEATURE:
<223> OTHER INFORMATION: Derivative of PTH polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Homoarginine

<400> SEQUENCE: 16

Xaa Val Xaa Glu Ile Gln Leu Met His Gln Xaa
1               5                   10

<210> SEQ ID NO 17
<211> LENGTH: 21
<212> TYPE: PRT
<213> ORGANISM: Homo sapiens

<400> SEQUENCE: 17

Ser Val Ser Glu Ile Gln Leu Met His Asn Leu Gly Lys His Leu Asn
1               5                   10                  15

Ser Met Glu Arg Val
            20

<210> SEQ ID NO 18
<211> LENGTH: 21
<212> TYPE: PRT
<213> ORGANISM: Rattus sp.

<400> SEQUENCE: 18

```
Ala Val Ser Glu Ile Gln Leu Met His Asn Leu Gly Lys His Leu Ala
1               5                   10                  15

Ser Val Glu Arg Met
            20

<210> SEQ ID NO 19
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: VARIANT, MOD_RES
<222> LOCATION: (1)..(1)
<223> OTHER INFORMATION: alpha-helix stabilixing residue, desamino Gly,
      desamino Ser or desamino Ala
<220> FEATURE:
<221> NAME/KEY: VARIANT, MOD_RES
<222> LOCATION: (3)..(3)
<223> OTHER INFORMATION: alpha-helix stabilizing residue, Ala, or Ser
<220> FEATURE:
<221> NAME/KEY: VARIANT, MOD_RES
<222> LOCATION: (8)..(8)
<223> OTHER INFORMATION: Met or Nle
<220> FEATURE:
<221> NAME/KEY: VARIANT
<222> LOCATION: (10)..(10)
<223> OTHER INFORMATION: Ala, Gln or Asn
<220> FEATURE:
<221> NAME/KEY: VARIANT, MOD_RES
<222> LOCATION: (11)..(11)
<223> OTHER INFORMATION: Arg, Homoarginine or Leu
<220> FEATURE:
<221> NAME/KEY: VARIANT, MOD_RES
<222> LOCATION: (12)..(12)
<223> OTHER INFORMATION: alpha-helix-stabilizing residue, Ala or Gly
<220> FEATURE:
<221> NAME/KEY: VARIANT, MOD_RES
<222> LOCATION: (13)..(13)
<223> OTHER INFORMATION: alpha-helix-stabilizing residue or Lys
<220> FEATURE:
<221> NAME/KEY: VARIANT, MOD_RES
<222> LOCATION: (14)..(14)
<223> OTHER INFORMATION: alpha-helix-stabilizing residue, Trp or His
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 19

Xaa Val Xaa Glu Ile Gln Leu Xaa His Xaa Xaa Xaa Xaa Leu Xaa
1               5                   10                  15

Ser Xaa Xaa Arg Xaa Xaa Trp Leu Arg Lys Lys Leu Gln Asp Val His
            20                  25                  30
```

Asn Xaa

```
<210> SEQ ID NO 20
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANTT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 20

Xaa Val Ser Glu Ile Gln Leu Met His Asn Leu Gly Lys His Leu Xaa
1               5                   10                  15

Ser Xaa Xaa Arg Xaa Xaa Trp Leu Arg Lys Lys Leu Gln Asp Val His
            20                  25                  30

Asn Xaa

<210> SEQ ID NO 21
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (1)..(1)
<223> OTHER INFORMATION: desamino Ala
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
```

```
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 21

Xaa Val Xaa Glu Ile Gln Leu Met His Asn Leu Gly Lys His Leu Xaa
1               5                   10                  15

Ser Xaa Xaa Arg Xaa Xaa Trp Leu Arg Lys Lys Leu Gln Asp Val His
            20                  25                  30

Asn Xaa

<210> SEQ ID NO 22
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (1)..(1)
<223> OTHER INFORMATION: desamino Ser
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 22

Xaa Val Xaa Glu Ile Gln Leu Met His Asn Leu Gly Lys His Leu Xaa
1               5                   10                  15

Ser Xaa Xaa Arg Xaa Xaa Trp Leu Arg Lys Lys Leu Gln Asp Val His
            20                  25                  30

Asn Xaa

<210> SEQ ID NO 23
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
```

```
<222> LOCATION: (1)..(1)
<223> OTHER INFORMATION: desamino Gly
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 23

Xaa Val Xaa Glu Ile Gln Leu Met His Asn Leu Gly Lys His Leu Xaa
1               5                   10                  15
Ser Xaa Xaa Arg Xaa Xaa Trp Leu Arg Lys Lys Leu Gln Asp Val His
            20                  25                  30
Asn Xaa

<210> SEQ ID NO 24
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
```

```
<223> OTHER INFORMATION: Tyr or Phe
<220> FEATURE:
<221> NAME/KEY: MOD_RES
<222> LOCATION: (11)..(11)
<223> OTHER INFORMATION: Homoarginine

<400> SEQUENCE: 24

Xaa Val Xaa Glu Ile Gln Leu Met His Gln Xaa Gly Lys Trp Leu Xaa
1               5                   10                  15

Ser Xaa Xaa Arg Xaa Xaa Trp Leu Arg Lys Lys Leu Gln Asp Val His
            20                  25                  30

Asn Xaa

<210> SEQ ID NO 25
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 25

Xaa Val Xaa Glu Ile Gln Leu Met His Asn Leu Gly Lys His Leu Xaa
1               5                   10                  15

Ser Xaa Xaa Arg Xaa Xaa Trp Leu Arg Lys Lys Leu Gln Asp Val His
            20                  25                  30

Asn Xaa

<210> SEQ ID NO 26
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
```

```
<222> LOCATION: (11)..(11)
<223> OTHER INFORMATION: Homoarginine
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 26

Xaa Val Ala Glu Ile Gln Leu Met His Gln Xaa Ala Lys Trp Leu Xaa
 1               5                  10                  15

Ser Xaa Xaa Arg Xaa Xaa Trp Leu Arg Lys Lys Leu Gln Asp Val His
                20                  25                  30

Asn Xaa

<210> SEQ ID NO 27
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Homoarginine
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 27
```

-continued

```
Ala Val Xaa Glu Ile Gln Leu Met His Gln Xaa Ala Lys Trp Leu Xaa
1               5                   10                  15

Ser Xaa Xaa Arg Xaa Xaa Trp Leu Arg Lys Lys Leu Gln Asp Val His
            20                  25                  30

Asn Xaa
```

<210> SEQ ID NO 28
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (11)..(11)
<223> OTHER INFORMATION: Homoarginine
<220> FEATURE:
<221> NAME/KEY: VARIANT
<222> LOCATION: (16)..(16)
<223> OTHER INFORMATION: Ala or Asn
<220> FEATURE:
<221> NAME/KEY: VARIANT
<222> LOCATION: (18)..(18)
<223> OTHER INFORMATION: Met or Val
<220> FEATURE:
<221> NAME/KEY: VARIANT
<222> LOCATION: (19)..(19)
<223> OTHER INFORMATION: Arg or Glu
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 28

```
Ser Val Xaa Glu Ile Gln Leu Met His Gln Xaa Ala Lys Trp Leu Xaa
1               5                   10                  15

Ser Xaa Xaa Arg Xaa Xaa Trp Leu Arg Lys Lys Leu Gln Asp Val His
            20                  25                  30

Asn Xaa
```

<210> SEQ ID NO 29
<211> LENGTH: 34
<212> TYPE: PRT
<213> ORGANISM: Artificial
<220> FEATURE:
<223> OTHER INFORMATION: Derivative of PTH Polypeptide
<220> FEATURE:
<221> NAME/KEY: MOD_RES
<222> LOCATION: (1)..(1)
<223> OTHER INFORMATION: Aib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES

```
<222> LOCATION: (11)..(11)
<223> OTHER INFORMATION: Homoarginine
<220> FEATURE:
<221> NAME/KEY: VARIANT
<222> LOCATION: (21)..(21)
<223> OTHER INFORMATION: Met or Val
<220> FEATURE:
<221> NAME/KEY: VARIANT
<222> LOCATION: (22)..(22)
<223> OTHER INFORMATION: Gln or Glu
<220> FEATURE:
<221> NAME/KEY: VARIANT
<222> LOCATION: (34)..(34)
<223> OTHER INFORMATION: Tyr or Phe

<400> SEQUENCE: 29

Xaa Val Xaa Glu Ile Gln Leu Xaa His Gln Xaa Ala Lys Trp Leu Ala
1               5                   10                  15

Ser Val Arg Arg Xaa Xaa Trp Leu Arg Lys Lys Leu Gln Asp Val His
            20                  25                  30

Asn Xaa

<210> SEQ ID NO 30
<211> LENGTH: 34
<212> TYPE: PRT
<213> ORGANISM: Rattus sp.

<400> SEQUENCE: 30

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe

<210> SEQ ID NO 31
<211> LENGTH: 34
<212> TYPE: PRT
<213> ORGANISM: Homo sapiens

<400> SEQUENCE: 31

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```